United States Patent [19]

Rody et al.

[11] 4,250,268
[45] Feb. 10, 1981

[54] POLYSILYLESTERS HAVING A POLYALKYLPIPERIDINE AS PART OF THE POLYMER USEFUL AS LIGHT STABILIZERS FOR PLASTICS

[75] Inventors: Jean Rody, Basel; Michael Rasberger, Riehen, both of Switzerland

[73] Assignee: Ciba-Geigy Corporation, Ardsley, N.Y.

[21] Appl. No.: 964,443

[22] Filed: Nov. 28, 1978

Related U.S. Application Data

[60] Division of Ser. No. 896,676, Apr. 14, 1978, abandoned, which is a continuation of Ser. No. 793,708, May 4, 1977, abandoned.

[51] Int. Cl.$^3$ .............................................. C08G 77/26
[52] U.S. Cl. ..................................... 525/100; 525/106; 525/431; 525/452; 528/27
[58] Field of Search ................. 528/27; 525/100, 106, 525/431, 452

[56] References Cited

U.S. PATENT DOCUMENTS

| | | | |
|---|---|---|---|
| B 559,701 | 3/1976 | Tanikella et al. | 260/75 N |
| 3,383,365 | 5/1968 | Tate et al. | 260/75 NH |
| 3,640,928 | 2/1972 | Murayama et al. | 260/23 XA |
| 3,684,765 | 8/1972 | Matsui et al. | 260/45.8 N |
| 3,705,126 | 12/1972 | Matsui et al. | 260/45.8 N |
| 3,790,525 | 2/1974 | Murayama et al. | 260/45.8 NZ |
| 3,840,494 | 10/1974 | Murayama et al. | 260/45.8 N |
| 3,850,877 | 11/1974 | Cook | 260/45.8 N |
| 3,859,293 | 1/1975 | Murayama et al. | 260/45.8 A |
| 3,901,853 | 8/1975 | Tanikella | 528/308 |
| 3,904,581 | 9/1975 | Murayama et al. | 260/45.8 N |
| 3,929,804 | 12/1975 | Cook | 260/45.8 N |
| 3,939,168 | 2/1976 | Cook | 260/45.8 N |
| 3,940,363 | 2/1976 | Murayama et al. | 260/45.8 N |
| 3,941,744 | 3/1976 | Murayama et al. | 260/45.8 N |
| 3,974,127 | 8/1976 | Tanikella et al. | 8/168 C |
| 4,001,190 | 1/1977 | Tanikella et al. | 260/75 N |
| 4,021,432 | 5/1977 | Holt et al. | 260/45.8 N |

FOREIGN PATENT DOCUMENTS

| | | | |
|---|---|---|---|
| 2611208 | 7/1976 | Fed. Rep. of Germany | 260/45.8 N |
| 2200380 | 4/1974 | France . | |
| 1393616 | 5/1975 | United Kingdom | 260/45.8 N |

*Primary Examiner*—Maurice J. Welsh
*Attorney, Agent, or Firm*—Wenderoth, Lind & Ponack

[57] ABSTRACT

Condensation polymers or addition polymers which contain sterically hindered polyalkylpiperidine groups are proposed as light stabilizers for plastics. The polymers concerned are relatively low-molecular polymers and a difunctional derivative of a polyalkylpiperidine is additionally used for the manufacture of these. The piperidine radical can be present in the main chain or as a side group of the polymeric stabilizer. Polymeric stabilizers of this type do not tend to migrate out of the plastic or to be removed by extraction; they are therefore very permanent in use.

14 Claims, No Drawings

POLYSILYLESTERS HAVING A POLYALKYLPIPERIDINE AS PART OF THE POLYMER USEFUL AS LIGHT STABILIZERS FOR PLASTICS

This application is a division of application Ser. No. 896,676, filed Apr. 14, 1978 now abandoned, which application is in turn a continuation of application Ser. No. 793,708, filed May 4, 1977 now abandoned.

The invention relates to polymeric compounds which can be used as light stabilisers for plastics. These compounds are condensation polymers and addition polymers which contain a sterically hindered polyalkylpiperidine radical.

It is known that derivatives of polyalkylpiperidines and above all those derivatives which are substituted in the 4-position, are very effective light stabilisers for plastics. Examples thereof are the ethers, esters and carbamates of 2,2,6,6-tetraalkylpiperidin-4-ols, such as are described in DT-OS Nos. 1,929,928, 2,204,659 and 2,258,752, the ketals of triacetoneamine, such as are described in DT-OS No. 2,203,533 and 2,211,177, the derivatives of 2,2,6,6-tetraalkyl-4-aminopiperidine, such as are described in DT-OS 2,040,975 and 2,349,962, spirohydantoins, such as are described in DT-OS Nos. 2,030,908, 1,769,646, 2,227,689 and 2,233,122, and 2,2,6,6-tetraalkylpiperidinyl-4-acetic acid derivatives, such as are described in DT-OS Nos. 2,337,847, 2,337,796 and 2,337,865. These light stabilisers are particularly valuable for polyolefines, styrene polymers and polyurethanes.

Tetramethylpiperidine itself and its simple derivatives, such as, for example, the 4-hydroxy compound or 4-acetoxy compound, are relatively volatile compounds which, in spite of a good light stabilising effect, are not used in practice for the stabilisation of plastics since they volatilise at the processing temperatures and also during prolonged outdoor storage of the stabilised plastics. Derivatives which have a somewhat higher molecular weight and still possess good solubility in the particular plastic, have proved valuable in practical use. For example, bis-tetramethylpiperidin-4-yl sebacate has proved valuable in the case of polypropylene. When the molecular weight is increased further, the solubility in the plastic decreases and, for example, tetrakis-tetramethylpiperidin-4-yl pyromellitate is insufficiently compatible with polypropylene even in concentrations of 0.25% and efflorescences occur after a short storage period.

It was therefore a surprising discovery that no efflorescence is observed when the molecular weight is further increased by using oligomeric or polymeric polyalkylpiperidine derivatives. On exposure to heat and also during prolonged storage, polymeric stabilisers of this type remain in the plastic to be protected, although they are not chemically incorporated.

A further advantage of these polymeric light stabilisers, as compared with monomeric light stabilisers of comparable structure, is their increased resistance to extraction.

The invention relates to condensation polymers and addition polymers, the recurrent molecular unit of which contains a polyalkylpiperidine radical of the formula

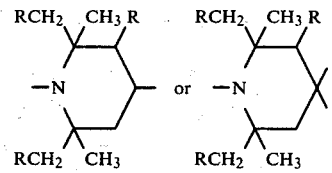

or is substituted by a polyalkylpiperidine side group of the formula

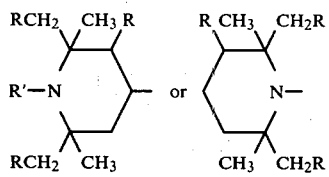

in which R denotes hydrogen or alkyl with 1–5 C atoms and R' denotes hydrogen, alkyl with 1–12 C atoms, alkenyl with 3–8 C atoms, alkinyl with 3–6 C atoms, aralkyl with 7–12 C atoms, alkanoyl with 1–8 C atoms or alkenoyl with 3–5 C atoms, and to copolymers with one another or with polyalkylpiperidine-free components.

Condensation polymers and addition polymers are to be understood as those polymers or oligomers which are manufactured by a polycondensation reaction or polyaddition reaction and possess hetero-atoms in the polymer chain. Examples of such polymers are polyesters, polyethers, polyamides, polyamines, polyurethanes, polyureas, polysulphides, polysulphones, polyimides, polysulphonates, polyphosphates, polyphosphonates, polysilyl esters, polysiloxanes, polyhydrazides, polyhydrazones or polybenzimidazoles.

The invention relates above all to polyesters, polyamides, polyurethanes, polyureas, polysilyl esters, polyethers, polyamines, polycarbonates and copolymers thereof, the recurrent molecular unit of which contains a polyalkylpiperidine radical of the formula

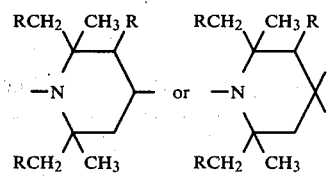

o is substituted by a polyalkylpiperidine side group of the formula

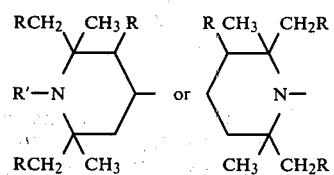

in which R denotes hydrogen or alkyl with 1–5 C atoms and R' denotes hydrogen, alkyl with 1–12 C atoms, allyl, benzyl, acetyl, acryloyl or crotonyl.

The invention relates above all to polyesters, polyamides, polyurethanes, polyureas, polysilyl esters and copolymers thereof, the recurrent molecular unit of which contains a polyalkylpiperidine radical of the formula

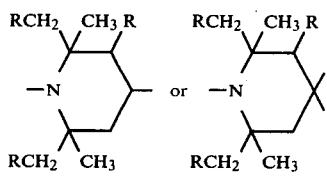

or is substituted by a polyalkylpiperidine side group of the formula

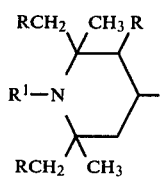

in which R denotes hydrogen or alkyl with 1–5 C atoms and R' denotes hydrogen, alkyl with 1–12 C atoms, allyl, benzyl, acetyl, acryloyl or crotonyl.

The invention relates in particular to compounds of the formulae I, Ia, II and III

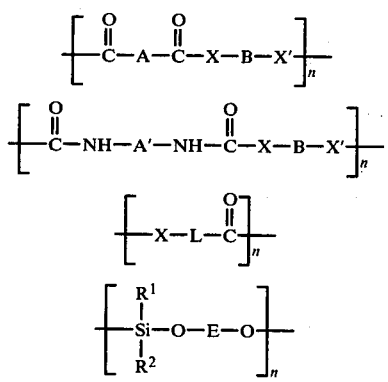

in which n denotes a value from 2 to about 50, X and X' denote oxygen or NY and Y denotes hydrogen, alkyl with 1–18 C atoms, cycloalkyl with 5–12 C atoms, aralkyl with 7–11 C atoms, aryl with 6–14 C atoms or a polyalkylpiperidine radical of the formula VIII

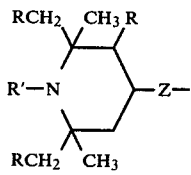

in which R and R' have the meaning given above and Z represents a direct bond, the group —CH$_2$CH$_2$— or the group —OCH$_2$CH$_2$CH$_2$—, R$^1$ and R$^2$ denote methyl, ethyl or phenyl and A, A', B, D and E denote divalent organic radicals, and, in each of the formulae I–III, at least one polyalkylpiperidine radical is present in the main chain or as a side group.

The invention also relates to compounds of the formulae IV, V and VI

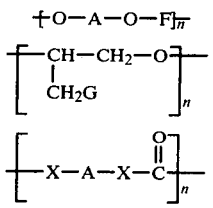

in which A, X and n have the meanings indicated above, F is a divalent organic radical which differs from A and G is a monovalent organic radical which contains a polyalkylpiperidine group, and, in each of the formulae IV to VI, at least one polyalkylpiperidine radical is present in the main chain or as a side group.

Finally, the invention also relates to the compounds of the formulae IV a and VII

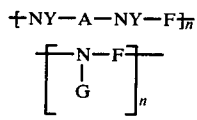

in which A, F, G, Y and n have the meanings indicated above, and, in each formula, at least one polyalkylpiperidine radical is present in the main chain or as a side group.

The index n indicates the average degree of polymerisation. Compounds with an index n=2–50 are to be regarded as oligomeric compounds or low-polymeric compounds, and their molecular weight in general does not exceed 10,000. Thus, they do not yet possess the material properties of high polymers, which would make it of interest to use them as a plastic. Depending on the structure, they are brittle or soft resins or viscous masses which can flow at room temperature.

When X and X' are oxygen, the compounds of the formula I and II represent polyesters, and when X and X' are NY they are polyamides. When X and X' are oxygen, the compounds of the formula Ia represent polyurethanes; when X and X' are NY, they are polyureas; and when X is NY and X' is oxygen, they are polyurethane-ureas. The compounds of the formula III represent polysilyl esters. The compounds of the formula IV and V represent polyethers. The compounds of the formula VI represent polycarbonates or polyureas depending on whether X denotes oxygen or NY. The compounds of the formulae IVa and VII represent polyamines. Amongst all the compounds which contain —NY— in the main chain, those in which Y is hydrogen are preferred.

When one of the radicals A, B, D, E or F contains an additional ether group, amine group, ester group, amide group, urethane group or urea group, the compounds can represent copolymers. When, for example, B in the formula I contains a urea group, the compounds of the formula I represent polyester-ureas or polyamide-ureas depending on the meaning of X and X'.

Another type of copolymer is formed by copolymerisation or copolycondensation of polyalkylpiperidine-containing monomers with polyalkylpiperidine-free monomers, it being possible to use up to 50 mol % of the latter. For example, an alternating copolymer

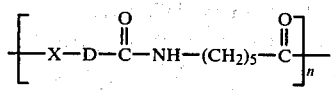

or a block copolymer

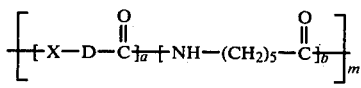

can be formed by the additional use of caprolactam in the manufacture of polymers of the formula II.

All these types of compounds can be linear or cyclic polymers or oligomers, and in most cases a mixture of both cyclic and linear compounds is formed under the customary methods of preparation. The cyclic compounds are free from end groups and the end groups contained in the linear compounds are predominantly the functional groups of the starting materials used for their preparation.

The compounds according to the invention are manufactured by the methods customary for condensation polymers and addition polymers, predominantly by a two-component polycondensation or two-component polyaddition in the case of the compounds of the formula I, Ia, III, IV, IVa, VI and VII and by one-component polycondensation or one-component polymerisation in the case of the compounds of the formula II and V. It is an essential feature of the invention that the components used for polycondensations or polyadditions are suitable derivatives of polyalkylpiperidines. In the case of two-component polycondensations or two-component polyadditions both components can be polyalkylpiperidine derivatives, or only one component is a polyalkylpiperidine derivative and the other component is a difunctional compound which is characteristic for the particular type and familiar to those skilled in the art. In the type of the formula III, only the component forming the unit E represents a polyalkylpiperidine derivative.

Whilst the invention in principle comprises all the components A, A', B, D, E, G and Y which contain polyalkylpiperidine groups, the following preferred sub-groups of compounds of the formulae I to VII result from the accessibility of corresponding polyalkylpiperidine derivatives.

Sub-group 1

Polyesters of the formula I, in which X and X' denote oxygen and A denotes one of the radicals of the formulae IX to XVII

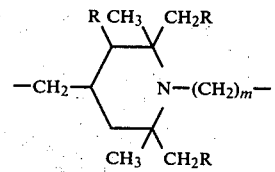

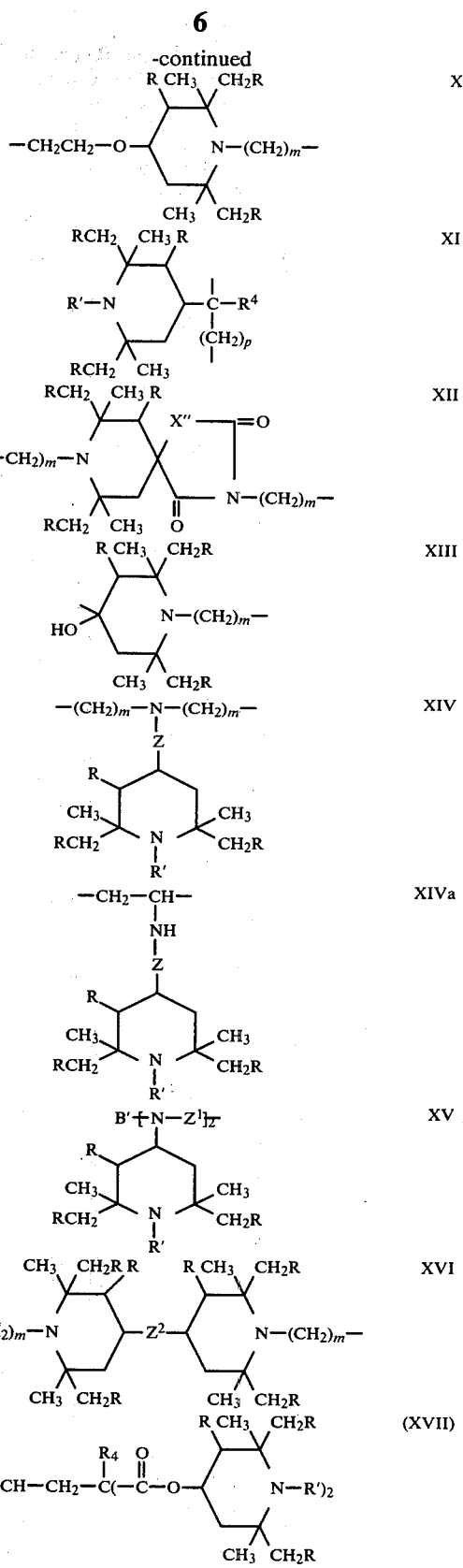

in which R denotes hydrogen or alkyl with 1-5 C atoms, R' denotes hydrogen, alkyl with 1-12 C atoms, allyl, benzyl, acetyl, acryloyl or crotonyl, m is 1, 2 or 3, p is nought or 1, preferably nought, $R^4$ denotes hydrogen, alkyl with 1-12 C atoms, allyl, benzyl or 3,5-di-tert.-butyl-4-hydroxybenzyl, X" is oxygen or preferably NH, Z denotes a direct bond or —CH$_2$CH$_2$— or —OCH$_2$CH$_2$CH$_2$—, $Z^1$ denotes —CH$_2$—, —CH$_2$CH$_2$— or —CO—$Z^{12}$— and $Z^{12}$ denotes one of the radicals —CH$_2$CH$_2$—, —(CH$_2$)$_3$—, —CH=CH—,

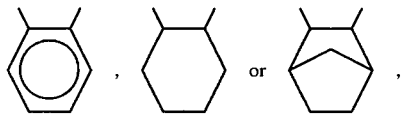

$Z^2$ denotes one of the radicals —N(R")—, —NR$^3$—CO—NR$^3$—, —NR$^3$—CO—CO—NR$^3$—, —NR$^3$—CO—Z$^3$—CO—NR$^3$—, alkylene with 4-10 C atoms, p-xylylene,

—O—alkylene—O— with 1-10 C atoms, —O—alkenylene—O— with 4-8 C atoms or —O—xylylene—O—, in which $R^3$ denotes hydrogen, alkyl with 1-12 C atoms, cyclohexyl, benzyl or aryl with 6-14 C atoms, but preferably H, R" denotes alkanoyl with 1-8 C atoms or alkenoyl with 3-5 C atoms and $Z^3$ denotes alkylene with 1-10 C atoms or phenylene, and B' represents an alkylene radical with 2-12 C atoms, a xylylene or hexahydroxylylene radical, a cyclohexylene or 4,4'-dicyclohexylmethane radical, an arylene radical with 6-12 C atoms or a -phenylene-$Z^4$-phenylene-radical, in which $Z^4$ denotes —CH$_2$—, C(CH$_3$)$_2$, —O— or —SO$_2$—, and in which B denotes an alkylene radical with 2-12 C atoms, an alkenylene radical with 4-8 C atoms, a xylylene or hexahydroxylylene radical, a cyclohexylene radical or a radical of the formula —CH$_2$CH$_2$OCH$_2$CH$_2$— or —CH$_2$CH$_2$O—phenylene—OCH$_2$CH$_2$—.

Polyesters of this type are prepared by a polycondensation reaction of the corresponding dicarboxylic acids of the formula HOOC—A—COOH or ester-forming derivatives thereof with customary diol components. Examples of dicarboxylic acids of this type are (a) 1-carboxyalkyl-polyalkylpiperidinyl-4-acetic acids.

Dicarboxylic acids of this type can be prepared by the known methods of carboxyalkylation, for example by a reaction of the corresponding NH compounds which are described in DT-OS No. 2,337,865, with chloroacetates, acrylates, acrylonitrile, β-bromopropionates or γ-chlorobutyrates and subsequent hydrolysis.

(b) 1-Carboxyallyl-4-(β-carboxyethoxy)-polyalkylpiperidines.

Dicarboxylic acids of this type can be prepared by a simultaneous or stepwise carboxyalkylation of the NH group and OH group of 4-hydroxy-polyalkylpiperidines by the methods described under (a).

(c) α-(Polyalkylpiperidinyl-4-)-malonic acids and alkyl, allyl or benzyl derivatives thereof.

These can be prepared by a Knoevenagel condensation of the corresponding 4-ketopiperidines with esters of malonic acid and subsequent hydrogenation, optionally with a subsequent alkylation, allylation, benzylation or hydroxybenzylation.

(d) Dicarboxylic acids of the formula HOOC—XII—COOH and their dialkyl esters can be prepared by simultaneous or stepwise carboxyalkylation of the corresponding NH compounds, such as are described, for example, in DT-OS No. 2,030,908.

(e) Acids of the formula HOOC-XIV-COOH can be prepared by reacting amines of the formula

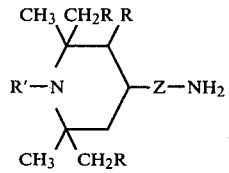

with 2 mols of chloroacetates, acrylates or acrylonitrile and subsequently hydrolysing the reaction product. Reaction of the same amines with dialkyl maleates gives the dialkyl esters of the acids of the formula HOOC—(XIVa)—COOH.

(f) Acids of the formula HOOC—XV—COOH can be prepared by reacting the diamines

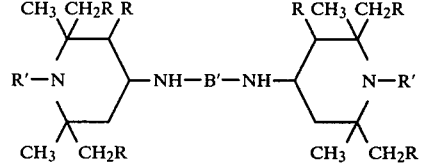

with 2 mols of a chloroacetate or of an acrylate or with 2 mols of a cyclic dicarboxylic acid anhydride.

(g) Acids of the formulae HOOC—XIII—COOH and HOOC—XVI—COOH can be prepared by carboxyalkylation of the corresponding NH compounds.

(h) Acids of the formula XVII(COOH)$_2$ can be prepared by a condensation reaction of a dialkyl malonate with formaldehyde and a malonate of the formula

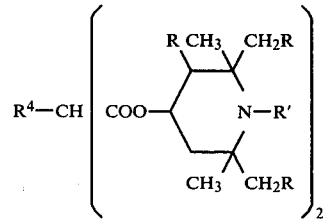

Ester-forming derivatives of dicarboxylic acids of this type are their esters, above all the lower alkyl esters such as, for example, the dimethyl or diethyl esters. The acid halides, above all acid chlorides, of the dicarboxylic acids are further ester-forming derivatives.

These dicarboxylic acids or ester-forming derivatives thereof are reacted with diols of the formula B(OH)$_2$ in which B has the above defined meaning. Examples of known diols of this type, such as are generally used in the preparation of polyesters, are ethylene glycol, 1,2-propylene glycol, 1,3-propylene glycol, butane-1,4-diol, hexane-1,6-diol, decane-1,10-diol, meta-xylylene glycol and para-xylylene glycol and their hydrogenation products, that is to say cyclohexane-1,3-diol and cyclohexane-1,4-diol, diethylene glycol or 1,3- or 1,4-di-(β-hydroxyethoxy)-benzene.

The reaction of the dicarboxylic acids—or derivatives thereof—with the diols is carried out in an approximate molar ratio of 1:1 by the various known methods of polycondensation. The relatively low-molecular polyesters predominantly carry hydroxyl groups and carboxyl groups or alkoxycarbonyl groups as the end groups.

Examples of polyesters of this type, in which the dicarboxylic acid radical A contains a polyalkylpiperidine radical are the compounds described by the following formulae:

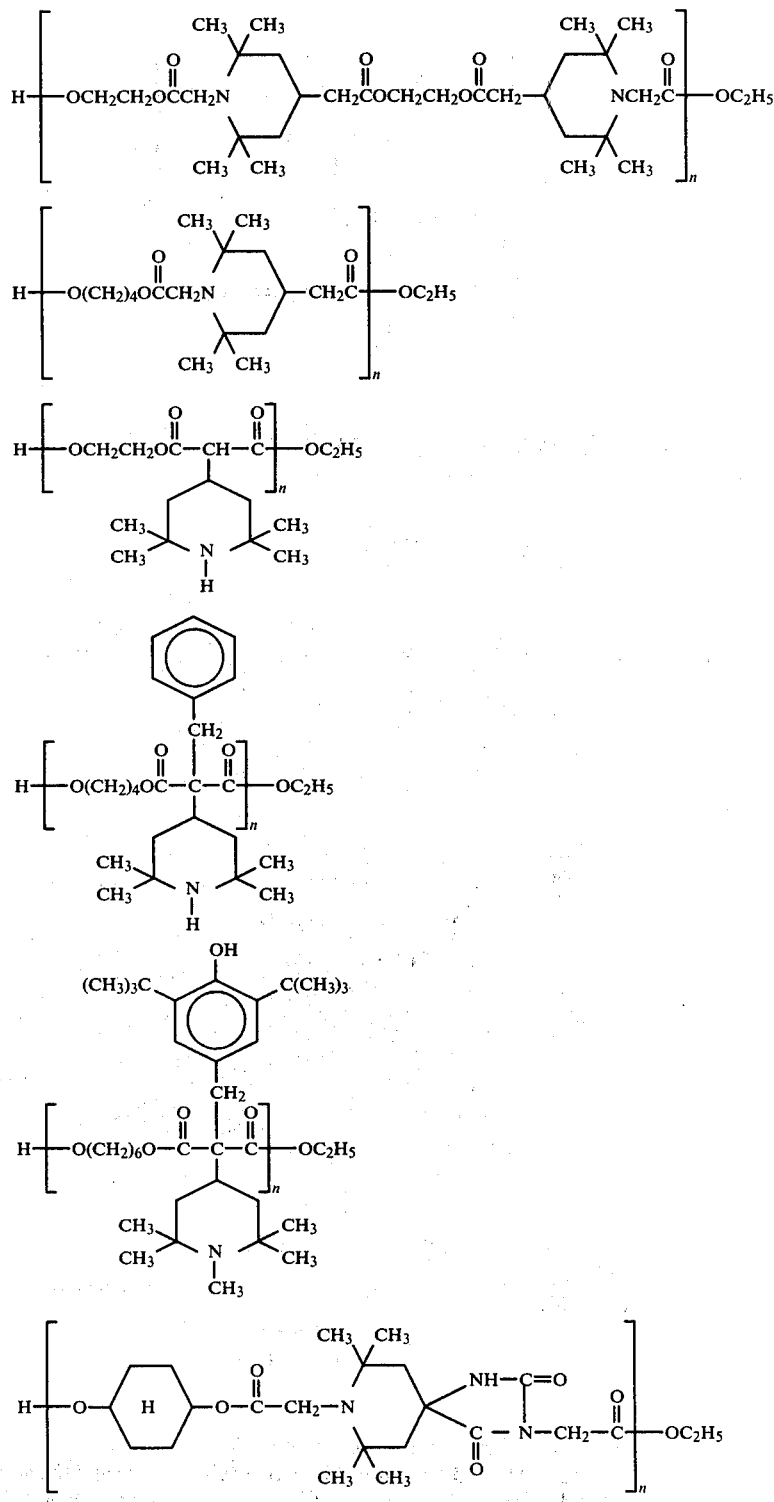

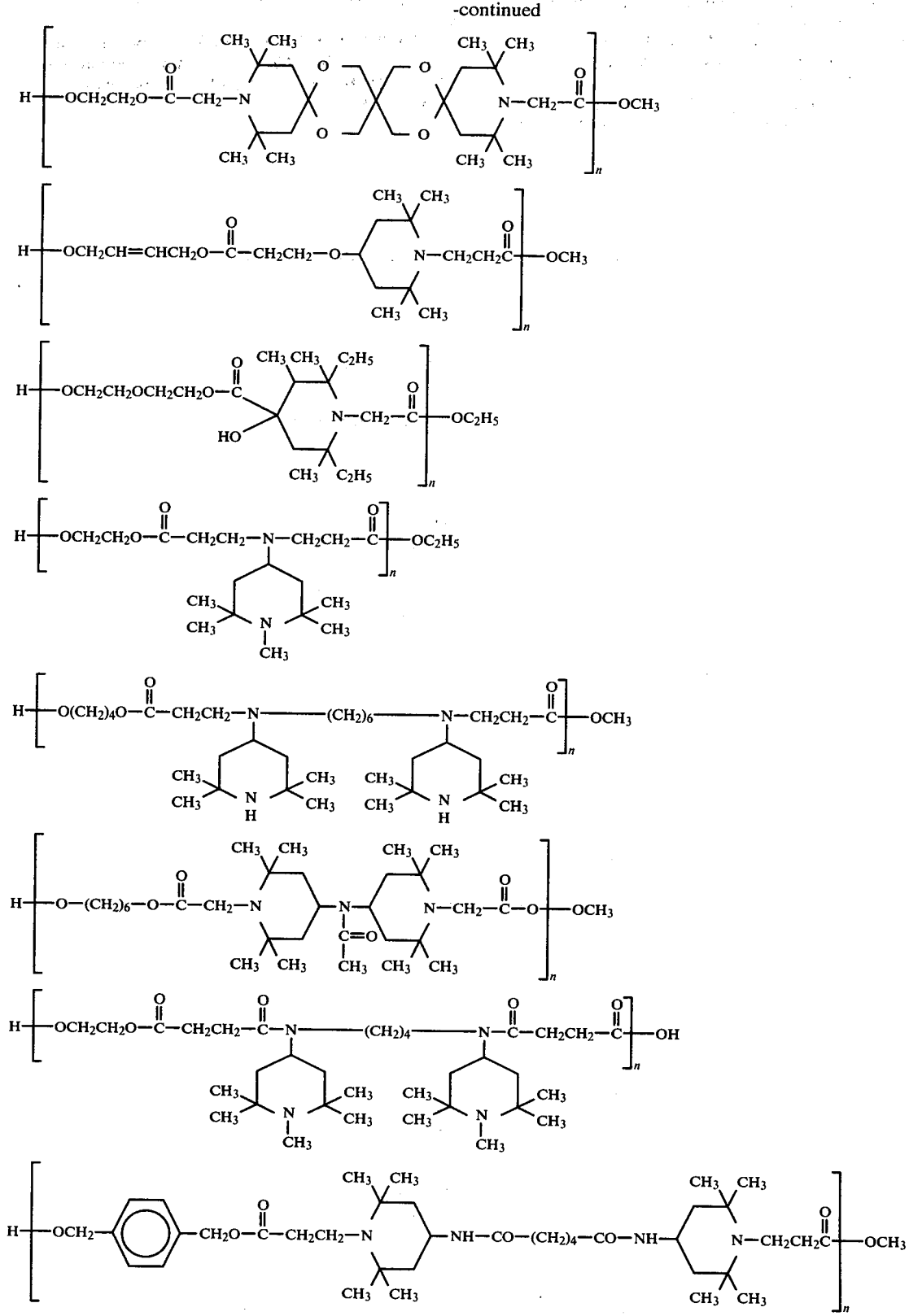
The last two formulae show examples of polyamide-esters such as those obtained by esterifying, in each case, one diamide-dicarboxylic acid with a diol.
Sub-group 2
Polyamides of the formula I in which X and X' denote NY and Y represents alkyl with 1–12 C atoms, cyclohexyl, benzyl or a polyalkylpiperidine radical of the formula VIII, but preferably represents hydrogen, A denotes one of the radicals of the formulae IX to XVII and B represents an alkylene radical with 2–12 C atoms, arylene with 6–12 C atoms, xylylene, hexahydroxylylene, a cyclohexylene or 4,4'-dicyclohexylmethane radical or a radical -phenylene-$Z^4$-phenylene- in which $Z^4$ can be —$CH_2$—, $<C(CH_3)_2$, —O— or —$SO_2$—.

These polyamides are prepared by a polycondensation reaction of polyalkylpiperidine-dicarboxylic acids, such as were listed in sub-group 1, or of amide-forming derivatives thereof, with diamine components of the formula $B(NHY)_2$. Examples of amide-forming derivatives of dicarboxylic acids are the esters or acid chlorides thereof, above all lower alkyl esters, for example the dimethyl or diethyl esters. Examples of diamines which can be used are ethylenediamine, 1,6-diaminohexane, 1,12-diaminododecane, m- and p-phenylene-diamine, 2,4-diaminotoluene, 4,4'-diaminodiphenylmethane, 4,4'-diaminodiphenyl ether, 4,4'-diaminodiphenylsulphone, p-xylylenediamine, 1,4-diaminocyclohexane, 4,4'-diamino-dicyclohexylmethane, N,N'-dimethyl-hexamethylenediamine, N-(2,2,6,6-tetramethylpiperidine-4yl)-hexamethylenediamine, N,N'-di-cyclohexyl-pentamethylenediamine, N,N'-bis-(2,2,6,6-tetra-methylpiperidine-4-yl)-hexamethylenediamine or N,N'-dimethyl-p-phenylenediamine. The reaction of the dicarboxylic acids—or derivatives thereof—with the diamines is carried out in an approximate molar ratio of 1:1 by the methods known for the preparation of polyamides. As long as the polyamides thus obtained are not cyclic, their end groups are predominantly amino groups and carboxyl groups or carbalkoxy groups.

Examples of polyamides of this type, in which the dicarboxylic acid radical A contains a polyalkylpiperidine radical, are the following compounds:

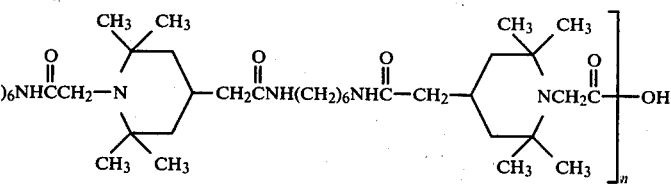

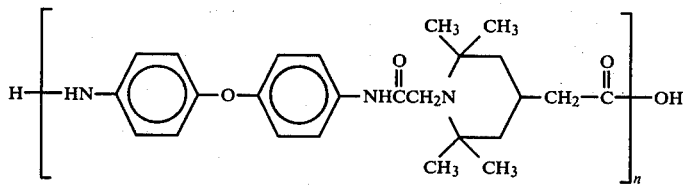

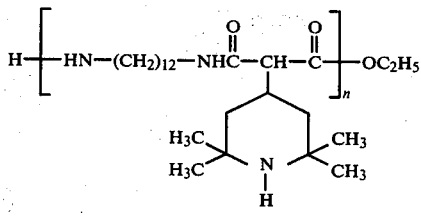

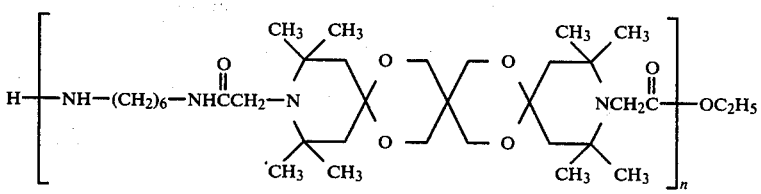

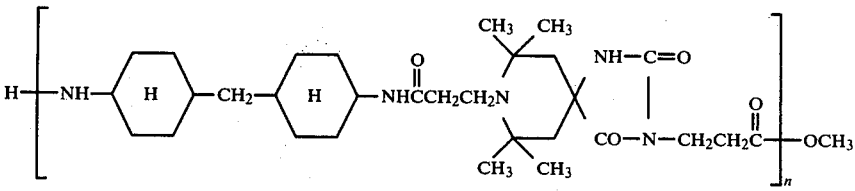

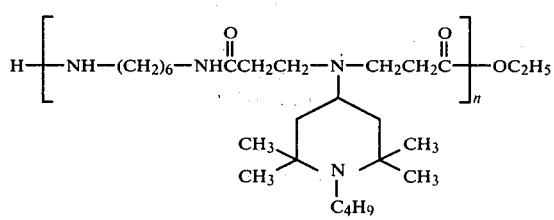
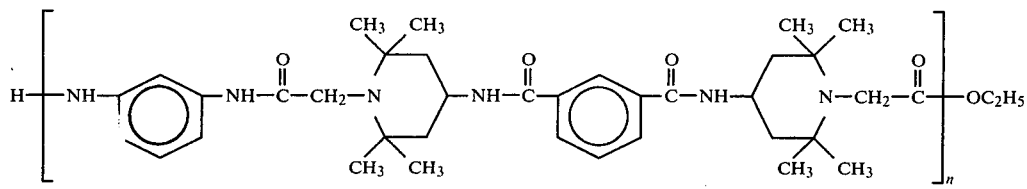
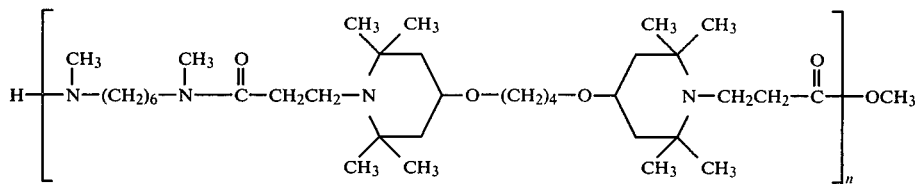
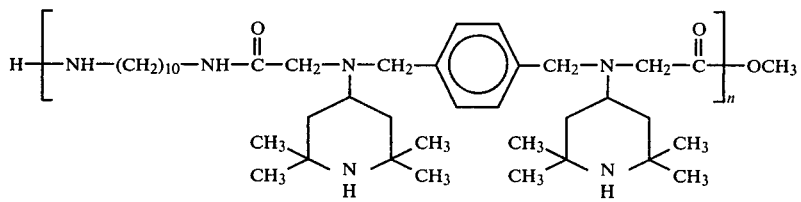
Sub-group 3
Polyesters of the formula I in which X and X' are oxygen, A denotes a direct bond, alkylene or phenyl-substituted, benzyl-substituted or hydroxydialkylbenzyl-substituted alkylene with 1-12 C atoms, arylene with 6-12 C atoms, cycloalkylene with 6-12 C atoms or a radical of the formulae IX to XVII and B represents one of the radicals of the formulae XVIII to XXX
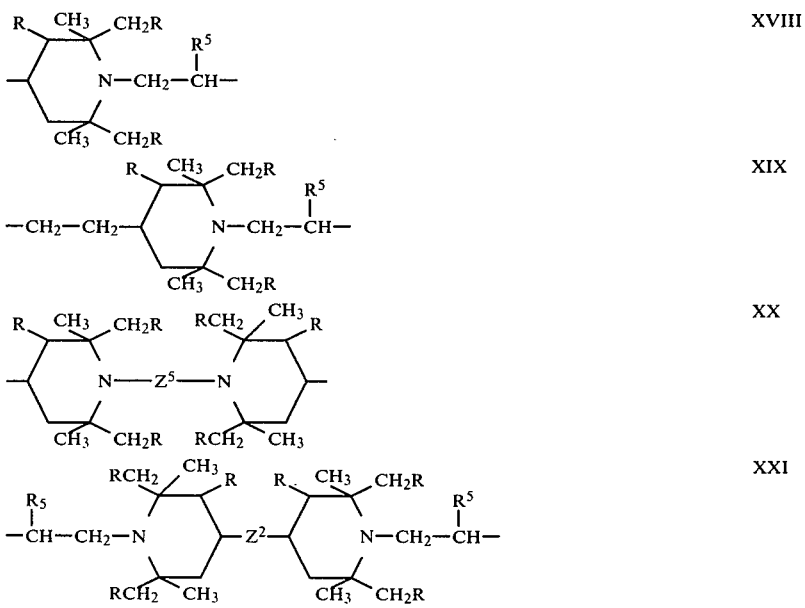

-continued
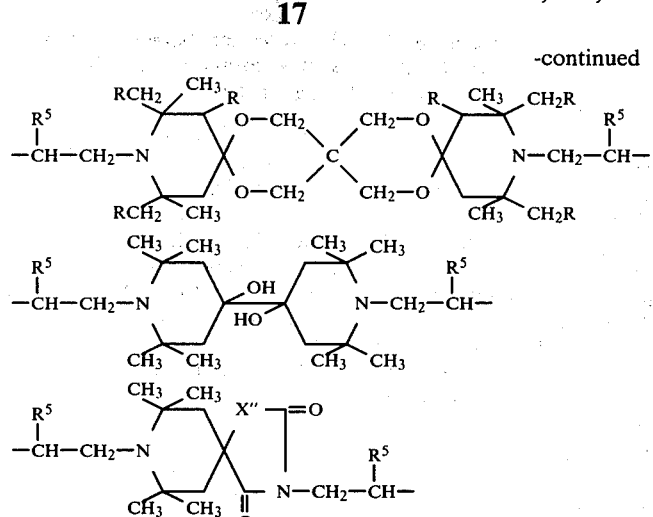
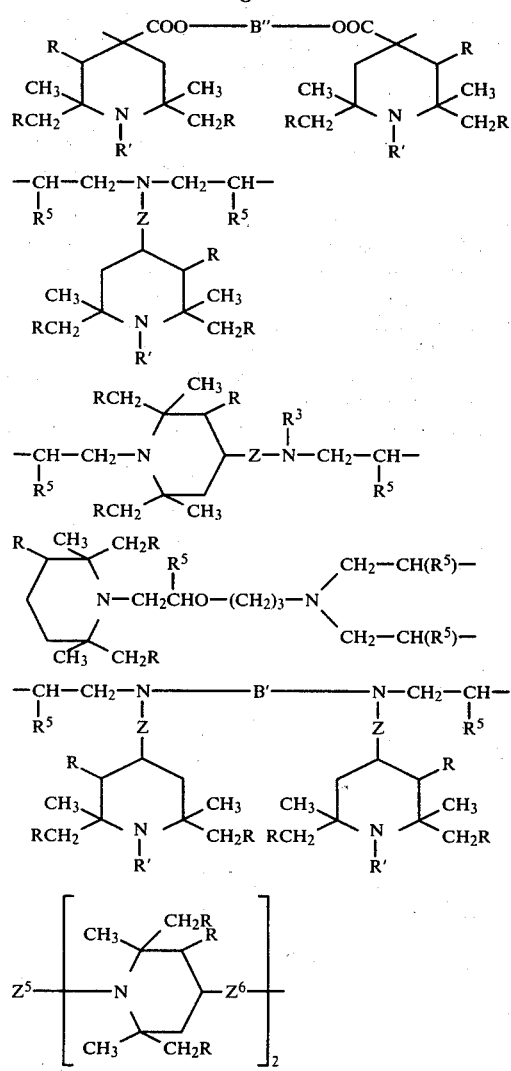
in which R, R', X'', $R^3$, Z, $Z^2$ and B' have the meanings indicated in sub-group 1, $R^5$ is hydrogen, methyl or phenyl, $Z^5$ represents alkylene or alkenylene with 4–8 C atoms, p-xylylene or a group of the formula
$-CH_2-\overset{R^5}{\underset{|}{CH}}-O-CO-NH-Z^7-NH-CO-O-\overset{R^5}{\underset{|}{CH}}-CH_2-$
or

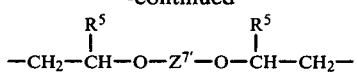

$Z^6$ represents one of the groups —CH$_2$CH$_2$—, —OCH$_2$CH(R$^5$)—, —N(R$^3$)—CH$_2$—CH(R$^5$)—, —CH$_2$CH$_2$—N(R$^3$)—CH$_2$CH(R$^5$)— or —O—(CH$_2$)$_3$—N(R$^3$)—CH$_2$CH(R$^5$)—, $Z^7$ is alkylene with 2-12 C atoms, arylene with 6-12 C atoms, 4,4'-dicyclohexylenemethane or a radical -phenylene-$Z^4$-phenylene- in which $Z^4$ has the meaning indicated in sub-group 1, $Z^{7'}$ denotes alkylene or alkenylene with 4-8 C atoms or p-xylylene and B" has the same meaning as B in sub-group 1.

These polyesters are prepared by a polycondensation reaction of customary dicarboxylic acids or of dicarboxylic acids containing polyalkylpiperidine, such as are listed under 1a-h, with diols of the formula HO—B—OH in which B corresponds to one of the formulae XVIII-XXX.

Diols of the formula HO—XIX—OH are described in DT-OS No. 2,402,636, diols of the formula HO—XX—OH are described in DT-OS No. 2,338,076, diols of the formula HO—XXI—OH are described in DT-OS No. 2,258,752 and No. 2,349,962, diols of the formula HO—XXII—OH are described in DT-OS No. 2,353,538, diols of the formula HO—XXII—OH are described in DT-OS No. 2,425,984 and diols of the formula HO—XXIV—OH are described in DT-OS No. 2,227,689.

The diols of the formula HO—XVIII—OH can be prepared by hydroxyalkylating the corresponding 4-hydroxypiperidines with ethylene oxide, propylene oxide or styrene oxide. Diols of the formula HO—XXV—OH can be prepared by transesterifying 4-hydroxy-4-alkoxycarbonyl-polyalkylpiperidines with diols of the formula HO—B"—OH. The diols of the formula HO—XXVI—OH, HO—XXVII—OH, HO—XXVIII—OH and HO—XXIX—OH can be prepared by N-hydroxyalkylation of the corresponding NH compounds by means of the epoxides

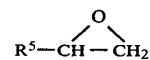

The diols of the formula HO—XXX—OH, in which $Z^5$ is —CH$_2$CH$_2$—, can be obtained by reducing the corresponding compounds in which $Z^5$ is —CH$_2$COO—alkyl. The compounds HO—XXX—OH in which $Z^5$ has the other meanings can be prepared by hydroxyalkylation of the corresponding NH compounds by means of the epoxides

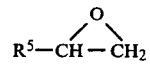

Examples of customary dicarboxylic acids are aliphatic, aromatic or cycloaliphatic carboxylic acids, such as, for example, succinic, adipic, sebacic, phenylmalonic, dibenzylmalonic, octylsuccinic, isophthalic, terephthalic or hexahydroterephthalic acid. In place of the free carboxylic acids, their ester-forming derivatives, above all the lower alkyl esters thereof, can be used.

When diols of the formula XX, XXI or XXX, in which $Z^2$ or $Z^5$ contains a urea, amide or urethane group, are used, the resulting polyesters represent mixed types, such as poly-urea-esters, poly-amide-esters or poly-urethane-esters. Polyesters which have the structures XXVI to XXIX are polyamide-esters.

Examples of polyesters in which the diol radical B contains a polyalkylpiperidine radical are the polyesters represented by the following formulae, and mixed types thereof.

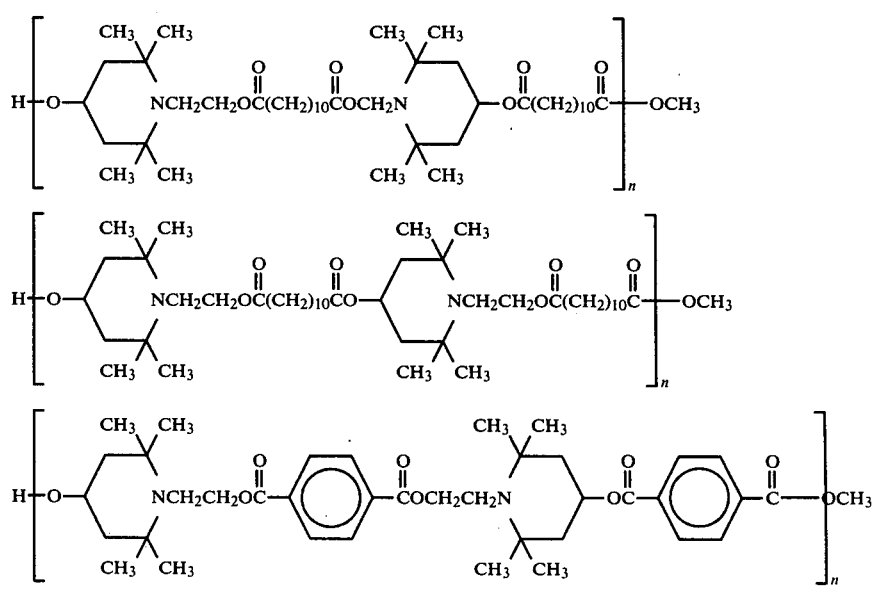

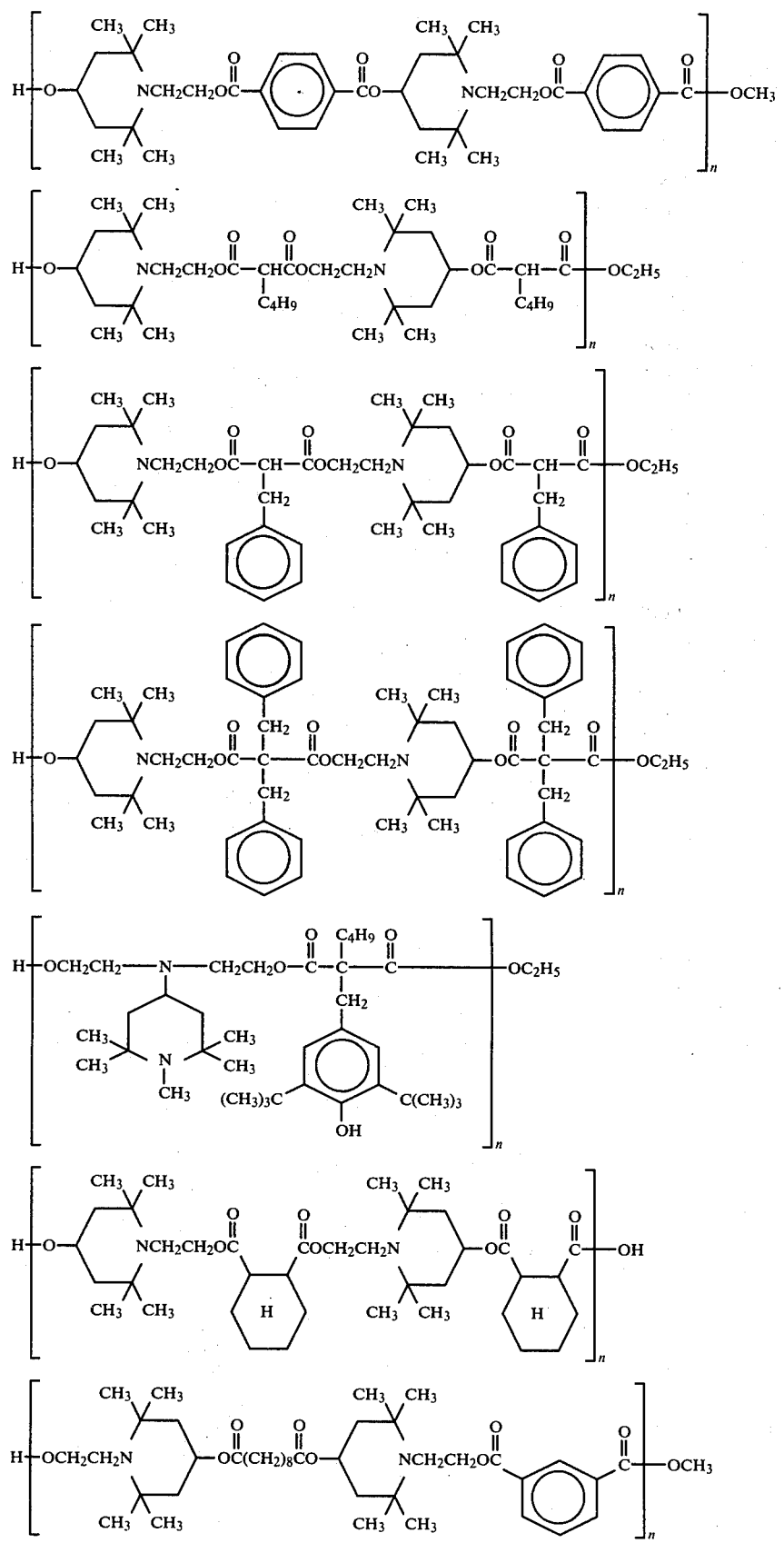

-continued
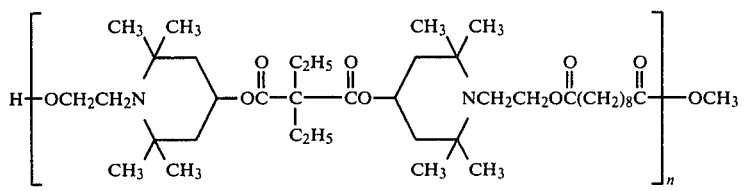
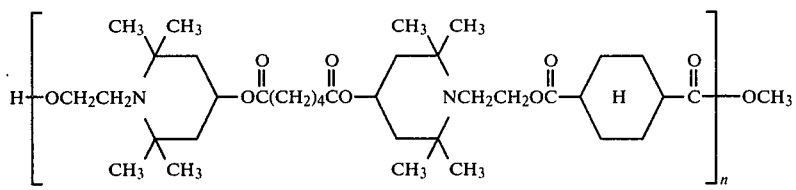
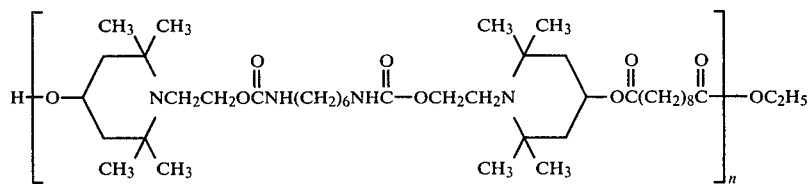
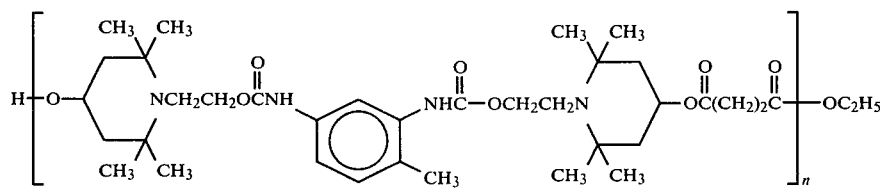
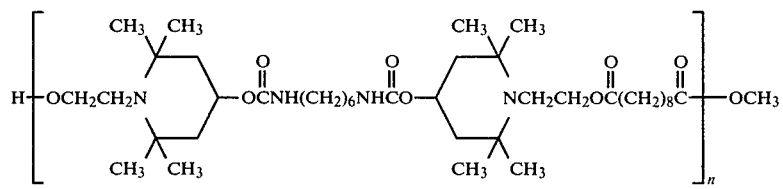
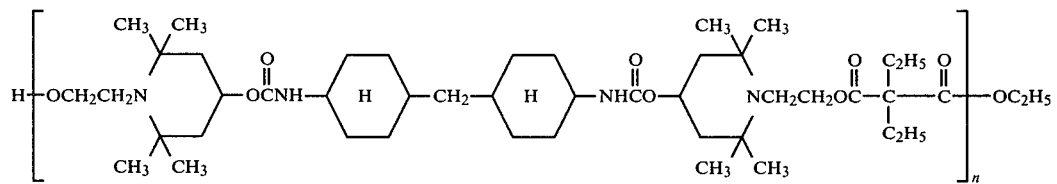
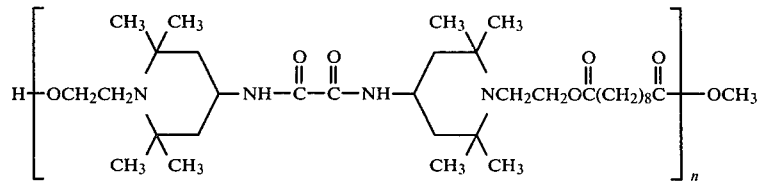
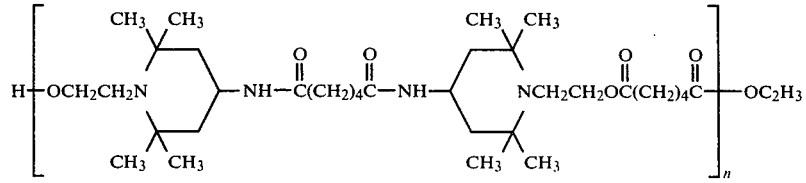

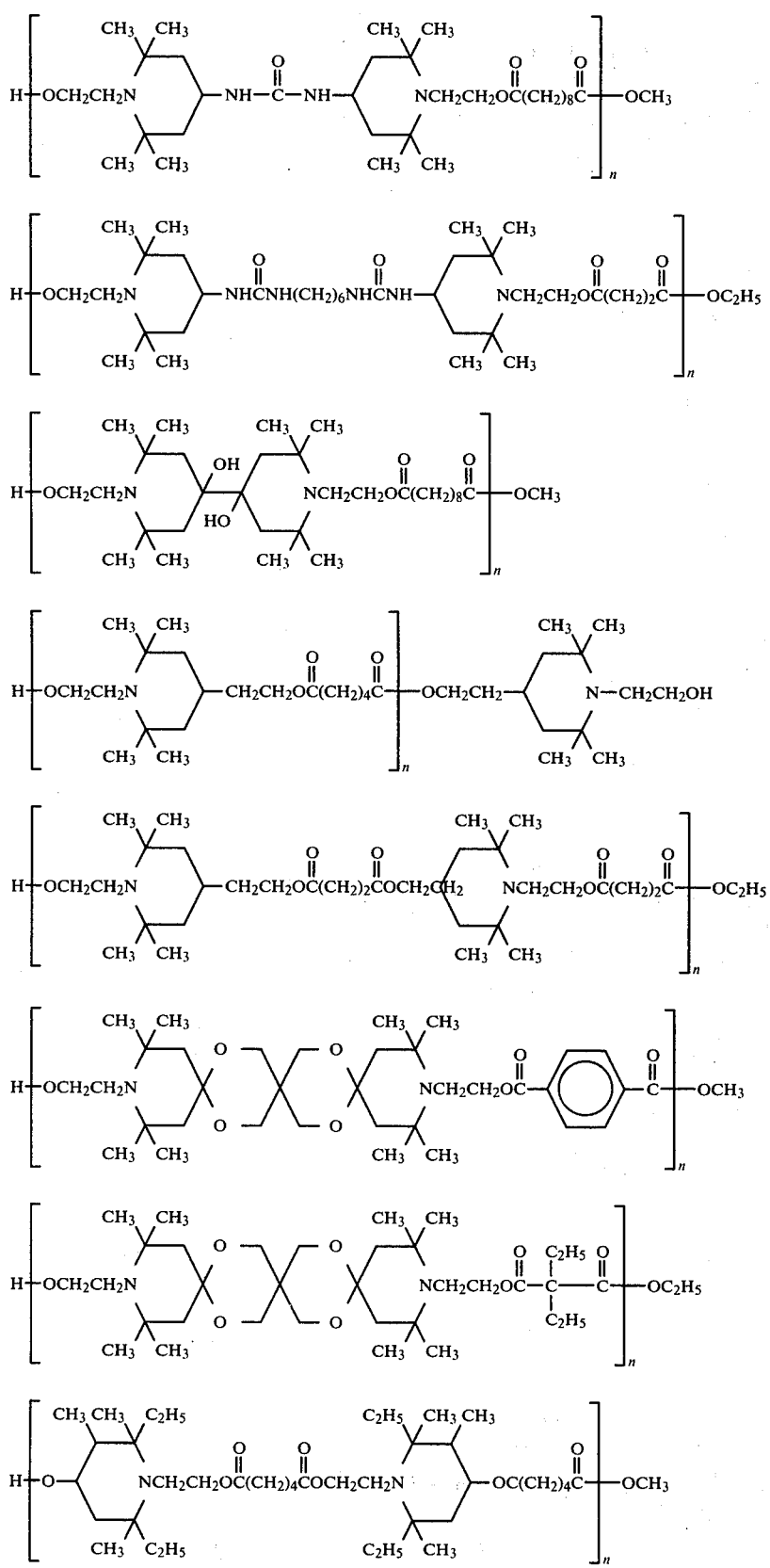

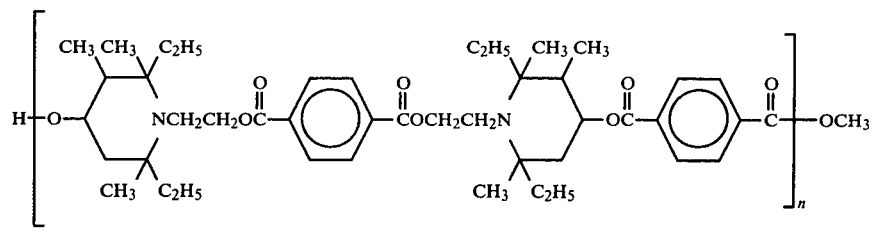
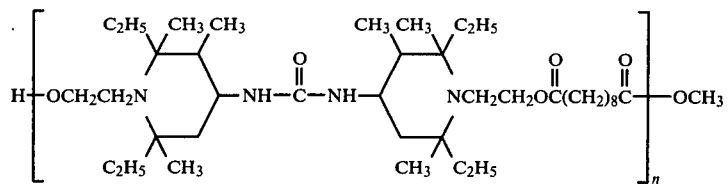
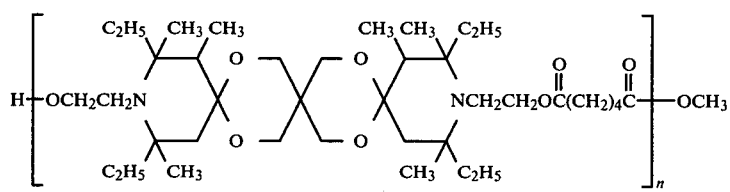
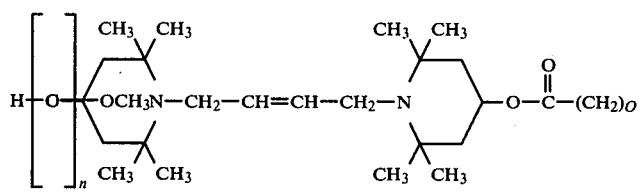
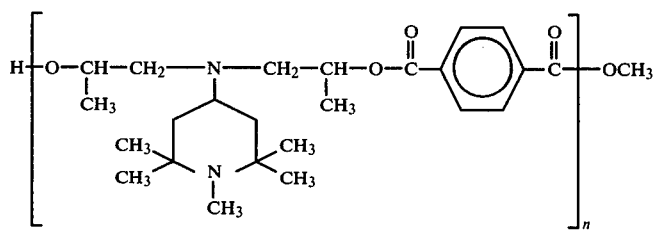
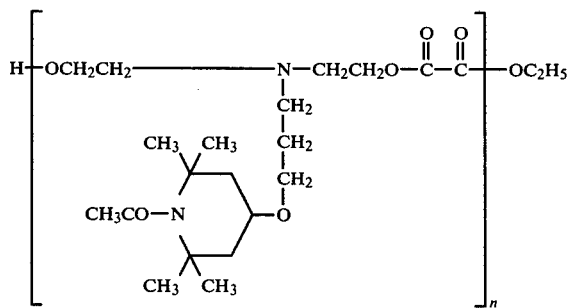
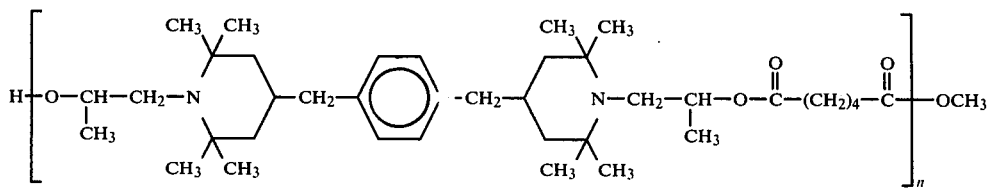

-continued
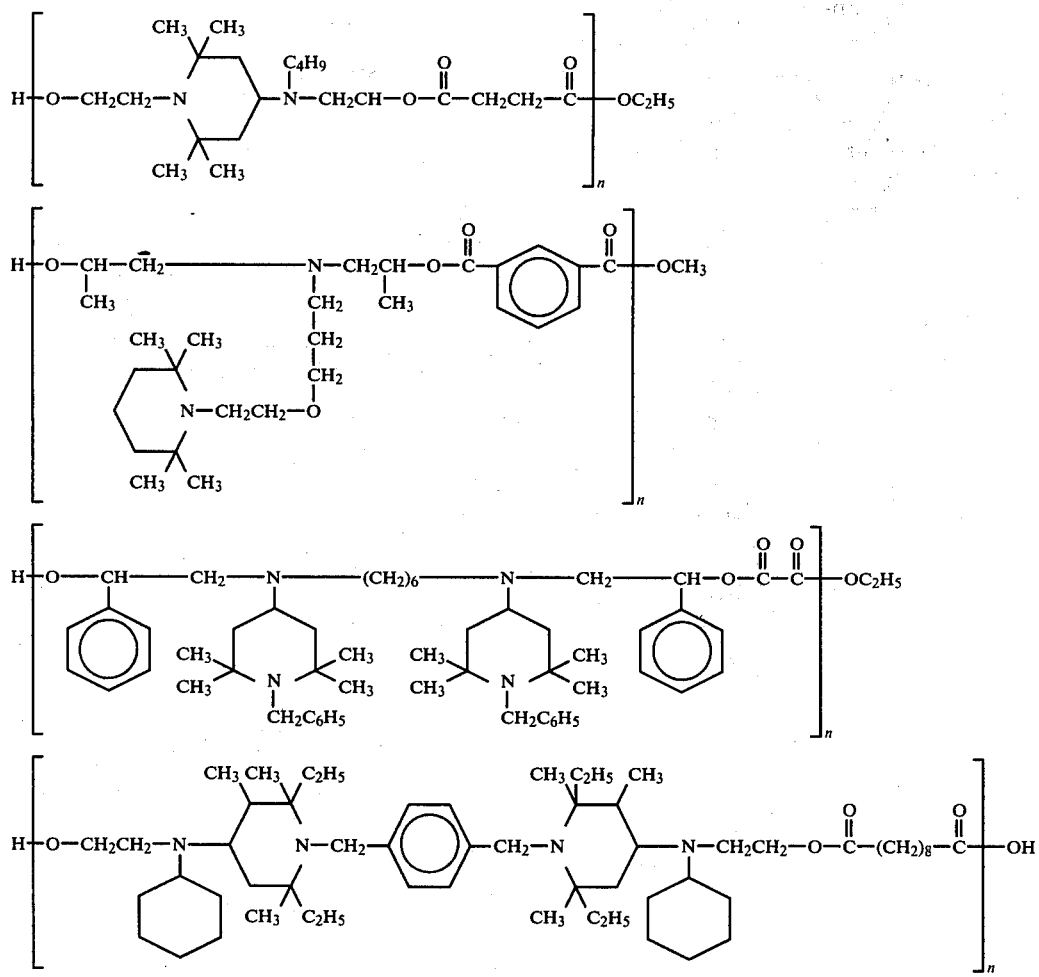
Sub-group 4
Polyamides of the formula I in which X and X' are NY and preferably NH, A has the same meaning as in sub-group 3 and B denotes one of the radicals XXXI to XXXIX
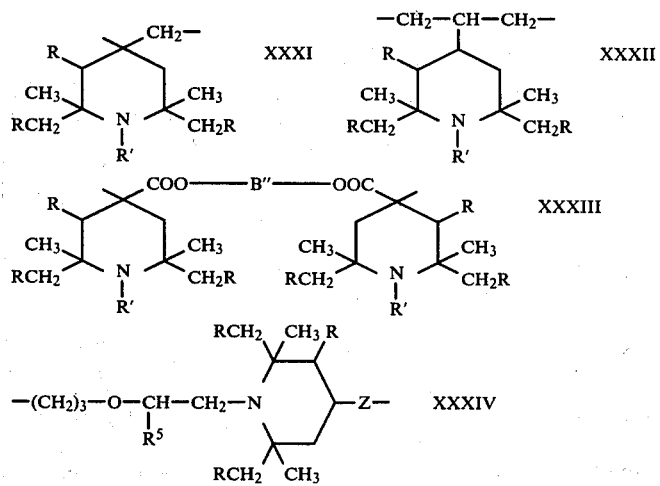

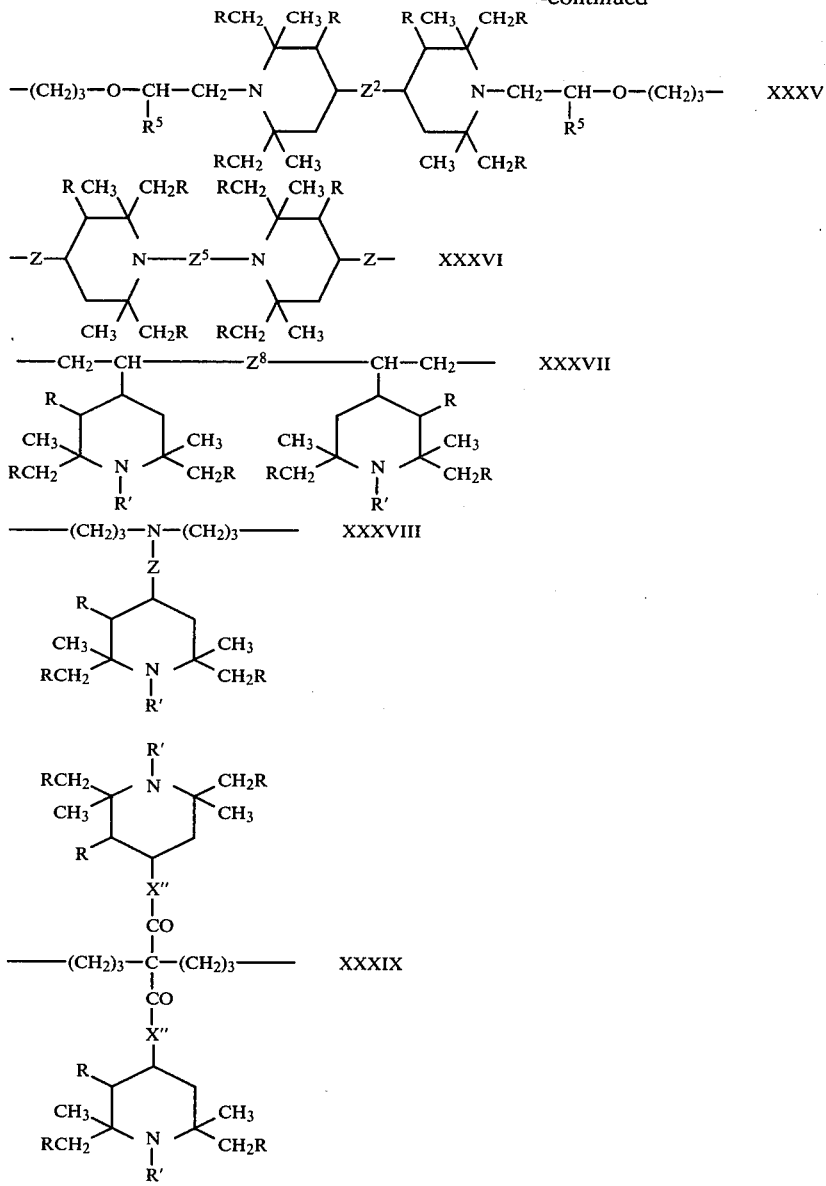

in which R, R', Z and $Z^2$ have the meaning indicated in sub-group 1 and B", $R^5$ and $Z^5$ have the meaning indicated in sub-group 3, $Z^8$ denotes an alkylene radical with 1–6 C atoms or phenylene and X" denotes oxygen or NH.

These polyamides are prepared by a polycondensation reaction of customary dicarboxylic acids, such as were mentioned under 3), or of dicarboxylic acids containing polyalkylpiperidine, such as were listed under 1a–h, or of the amide-forming derivatives thereof with diamines of the formula

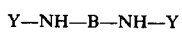

in which B corresponds to one of the formulae XXXI to XXXIX.

Diamines of the formula YNH—XXXI—NHY can, for example, be prepared from the piperidinone-4-cyanohydrins described in Japanese Pat. No. 640,258, by reductive amination.

Diamines of the formula YNH—XXXII—NHY can be prepared by a Knoevenagel condensation of the corresponding 4-oxopiperidines with malodinitrile and subsequent hydrogenation.

Diamines of the formula $H_2N$—YNH—XXXIII—NHY—$NH_2$ can be prepared by a trans-esterification of 4-amino-4-alkoxycarbonylpolyalkylpiperidines with diols of the formula HO—B"—OH.

Diamines of the formulae YNH—XXXIV—NHY and YNH—XXXV—NHY can be prepared by cyanoethylation of the corresponding dihydroxy compounds and subsequent hydrogenation of the reaction product and the compounds YNH—XXXVI—NHY in which Z is —$OCH_2CH_2CH_2$—, can be prepared in the same way. Diamines of the formula YNH—XXXVII—NHY can be prepared by a condensation reaction of 4-oxopiperidines with dinitriles of the formula NC—$CH_2$—$Z^7$—$CH_2$—CN and hydrogenation of the bis-azomethines.

Diamines of the formula YNH—XXXVIII—NHY can be prepared by cyanoethylation of the corresponding primary amines and subsequent hydrogenation of the reaction products.

Diamines of the formula YNH—XXXIX—NHY can be prepared by cyanoethylation of the corresponding malonates or malonic acid amides and subsequent hydrogenation of the dinitriles.

In the case of the diamine syntheses mentioned in which the final step is the hydrogenation of a dinitrile, the primary diamines (Y=H) are usually formed. Secondary diamines in which Y is not hydrogen can be obtained either by adding a suitable monooxo compound during the hydrogenation or by converting the primary diamine into a secondary diamine by customary methods of N-substitution.

The compounds of the formula I in which X is NY and X' is NH or NY, A has the same meaning as in sub-group 4, B has the same meaning as in sub-group 2 and Y is a polyalkylpiperidine radical of the formula XL,

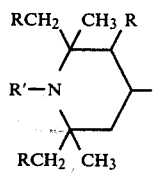   XL in which R and R' have the same meaning as in sub-group 1, are a special category of polyamides.

These polyamides are prepared by a polycondensation reaction of customary dicarboxylic acids with diamines of the formula

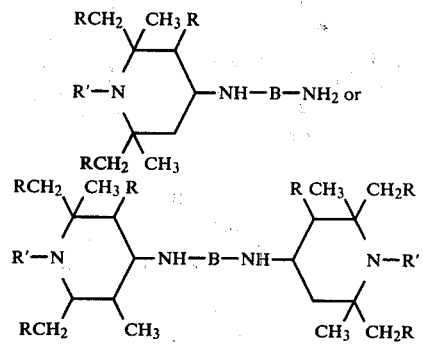

wherein B has the meaning indicated above.

Diamines of this type can be prepared from the corresponding 4-oxopiperidines by hydrogenation in the presence of diamines of the formula $H_2N$—B—$NH_2$ and in the presence of customary hydrogenation catalysts.

Examples of polyamides of the sub-group 4 are the following formulae:

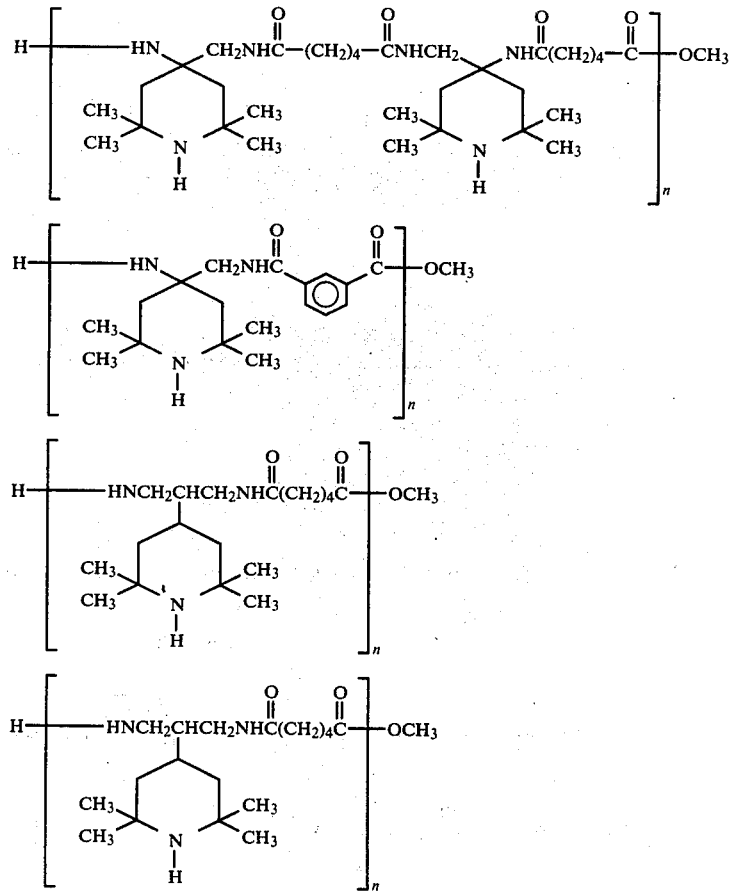

-continued
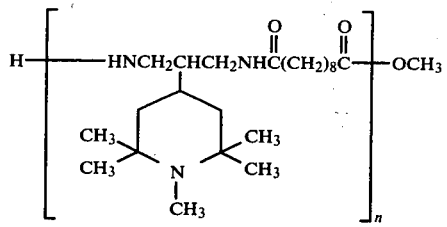
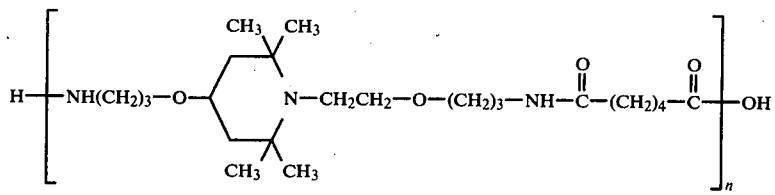
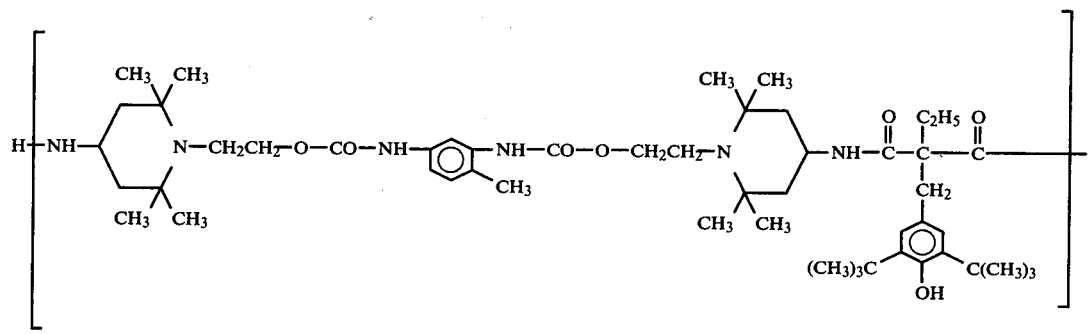
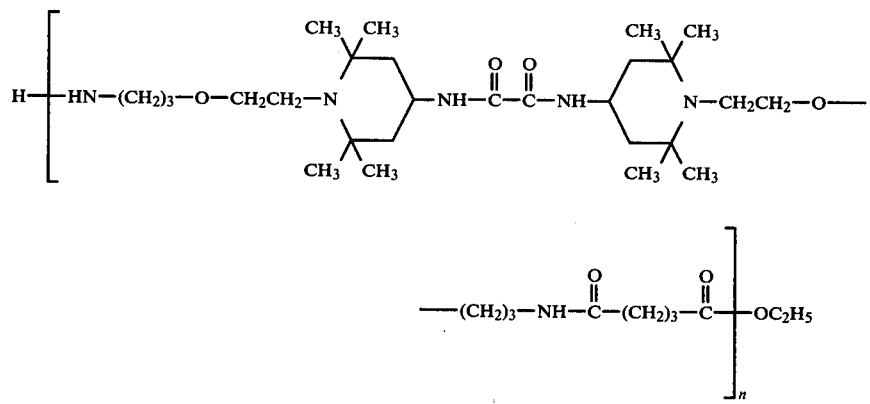
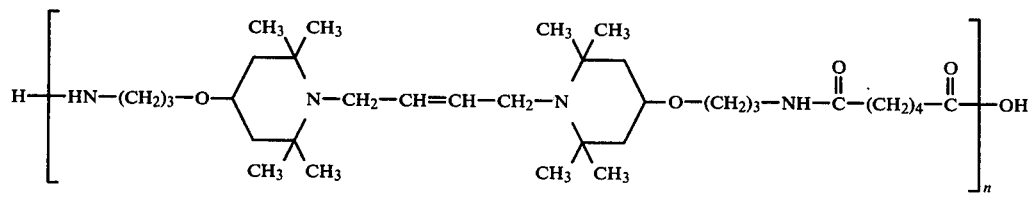
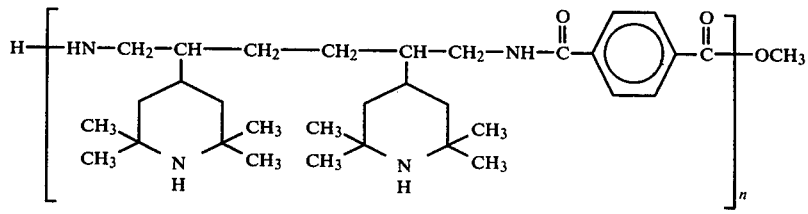

-continued
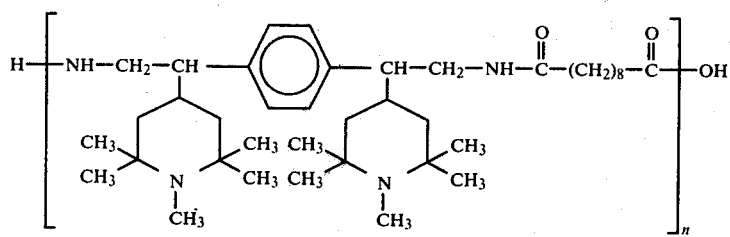
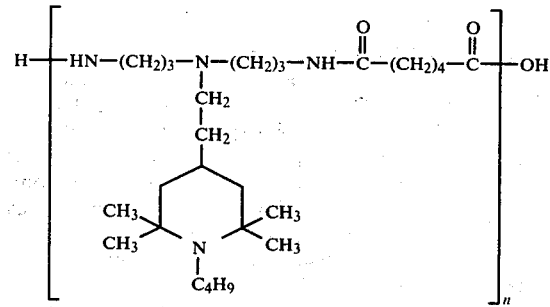
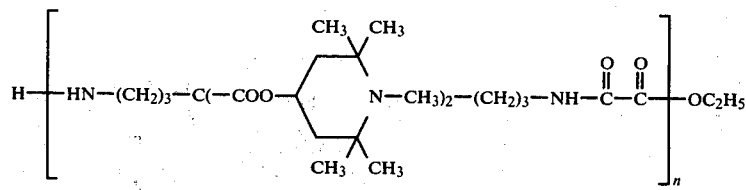
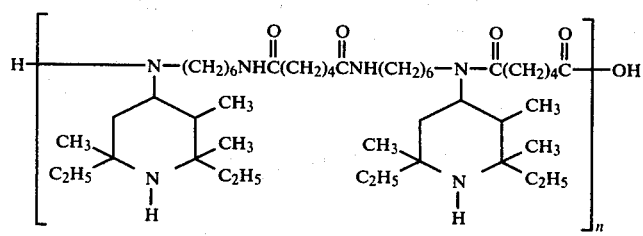
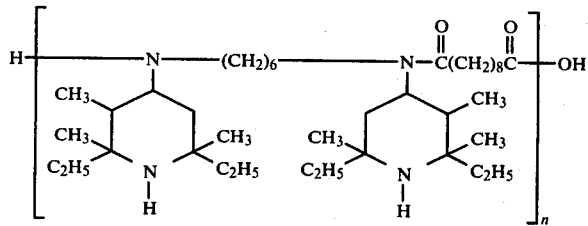
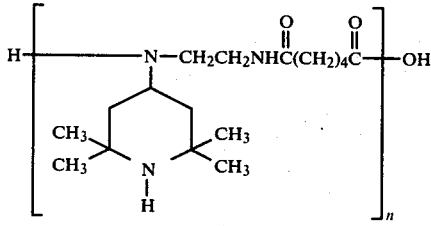
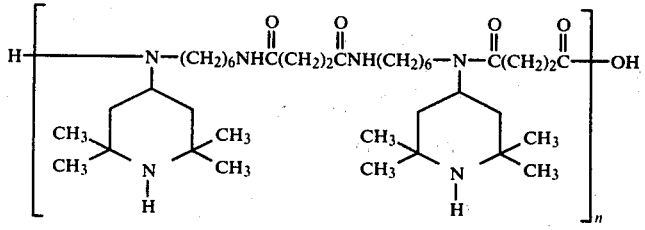

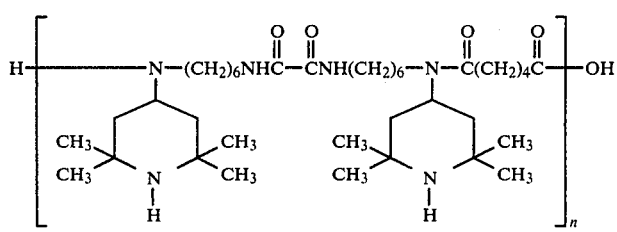

Sub-group 5

Polyurethanes of the formula Ia in which X and X' are oxygen, A' has the same meaning as $Z^7$ in sub-group 3 and B has the same meaning as in sub-group 3.

These polyurethanes can be prepared by a polyaddition reaction of a diisocyanate OCN—A'—NCO with a diol HO—B—OH in an approximate molar ratio of 1:1.

Sub-group 5a

Polyureas of the formula Ia in which X and X' are NY, A' has the same meaning as in sub-group 5, B either has the meaning of B in sub-groups 2 and 4 or the group —X—B—X'— denotes one of the following formulae XLI to XLIII.

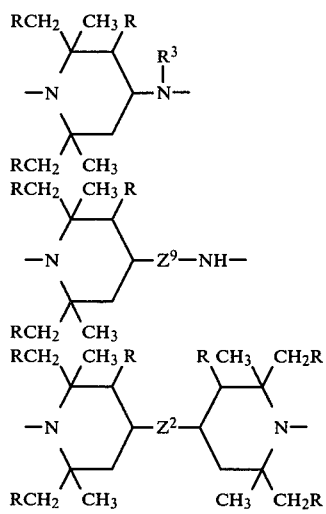

XLI

XLII

XLIII in which R, $R^3$ and $Z^2$ have the meanings indicated in sub-group 1 and Y has the meaning indicated in sub-group 2, $Z^9$ denotes —CH$_2$CH$_2$— or —OCH$_2$CH$_2$CH$_2$— and wherein at least one of the radicals B or Y contains a polyalkylpiperidine radical.

These polyureas can be prepared by a polyaddition reaction of a diisocyanate OCN—A'—NCO with a diamine of the formula YNH—B—NHY or H—XLI—H to H—XLIII—H in an approximate molar ratio of 1:1.

The 4-aminopiperidines H—XLI—H are described in DT-OS No. 2,040,975. The amines H—XLII—H can be prepared by hydrogenation of the corresponding 4-cyano- or 4-cyanoethoxy-piperidines.

The bis-piperidines H—XLIII—H, in which $Z^2$ is an alkylene or xylylene radical, can be prepared by a Wittig reaction of 4-oxopiperidines with alkylene diphosphonates or xylylene diphosphonates and subsequent hydrogenation of the resulting bis-dehydropiperidines. If $Z^2$ represents a group —NY—CO—NY—, —NY—CO—CO—NY or —NY—CO—$Z^3$—CO—NY, the bis-piperidines are described in DT-OS No. 2,040,975. The compounds H—XLIII—H, in which $Z^2$ represents —NH—, are also described in DT-OS No. 2,040,975. The corresponding N-acyl or N-alkyl derivatives can be obtained from these compounds by acylation or alkylation. The compounds H—XLIII—H, in which $Z^2$ is —O-alkylene-O—, can be prepared from the corresponding 4-hydroxypiperidines by reaction with an alylene dihalide and the corresponding alkenylene and xylylene compounds can be obtained analogously.

Sub-group 5b

Poly-urethane-ureas of the formula Ia in which X denotes NY and X' denotes oxygen, Y has the same meaning as in sub-group 2 and A' has the same meaning as in sub-groups 5 and 5a and B is an alkylene radical with 2–6 C atoms, or in which —X—B—X'— is one of the groups of the formulae XLIV to IL.

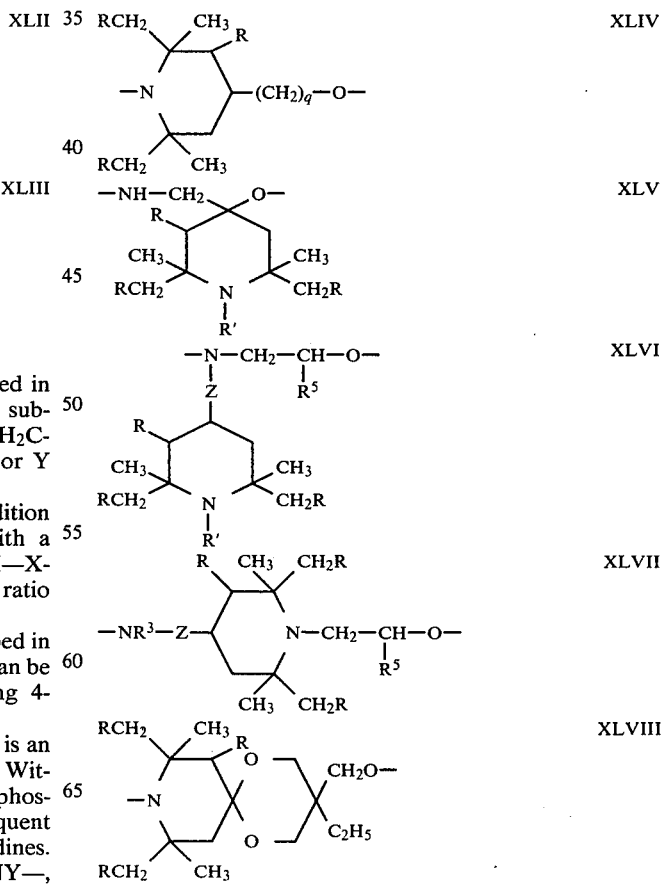

XLIV

XLV

XLVI

XLVII

XLVIII

-continued

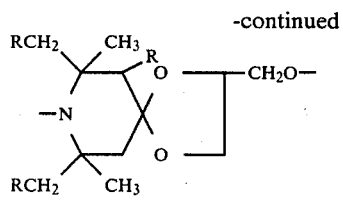

wherein q denotes nought or 2, Z and R³ have the same meaning as in sub-group 1 and R⁵ has the same meaning as in sub-group 3 and in which at least one of the radicals Y or B contains a polyalkylpiperidine radical.

Polymers of this type are prepared by reacting a diisocyanate QCN—A′—NCO with an amino-alcohol YNH—B—OH or H—XLIV—H to H—IL—H in an approximate molar ratio of 1:1.

When q=0, the compounds H—XLIV—H can be prepared by reduction of the corresponding 4-oxopiperidines. When q=2, the compounds are described in DT-OS No. 2,402,636. The amino-alcohols H—XLV—H can be prepared by hydrogenation of the corresponding cyanohydrins of 4-oxopiperidines.

The compounds H—XLVIII—H and H—IL—H are described in DT-OS No. 2,353,538.

The amino-alcohols H—XLVI—H can be prepared by hydroxyalkylation of the corresponding primary amines, whilst, in order to prepare the compounds H—XLVII—H, first the hydroxyalkyl group and then the R³NH—Z group are introduced into the 4-position of the piperidine radical.

Examples of polyadducts of the sub-groups 5, 5a and 5b are reproduced in the following formulae:

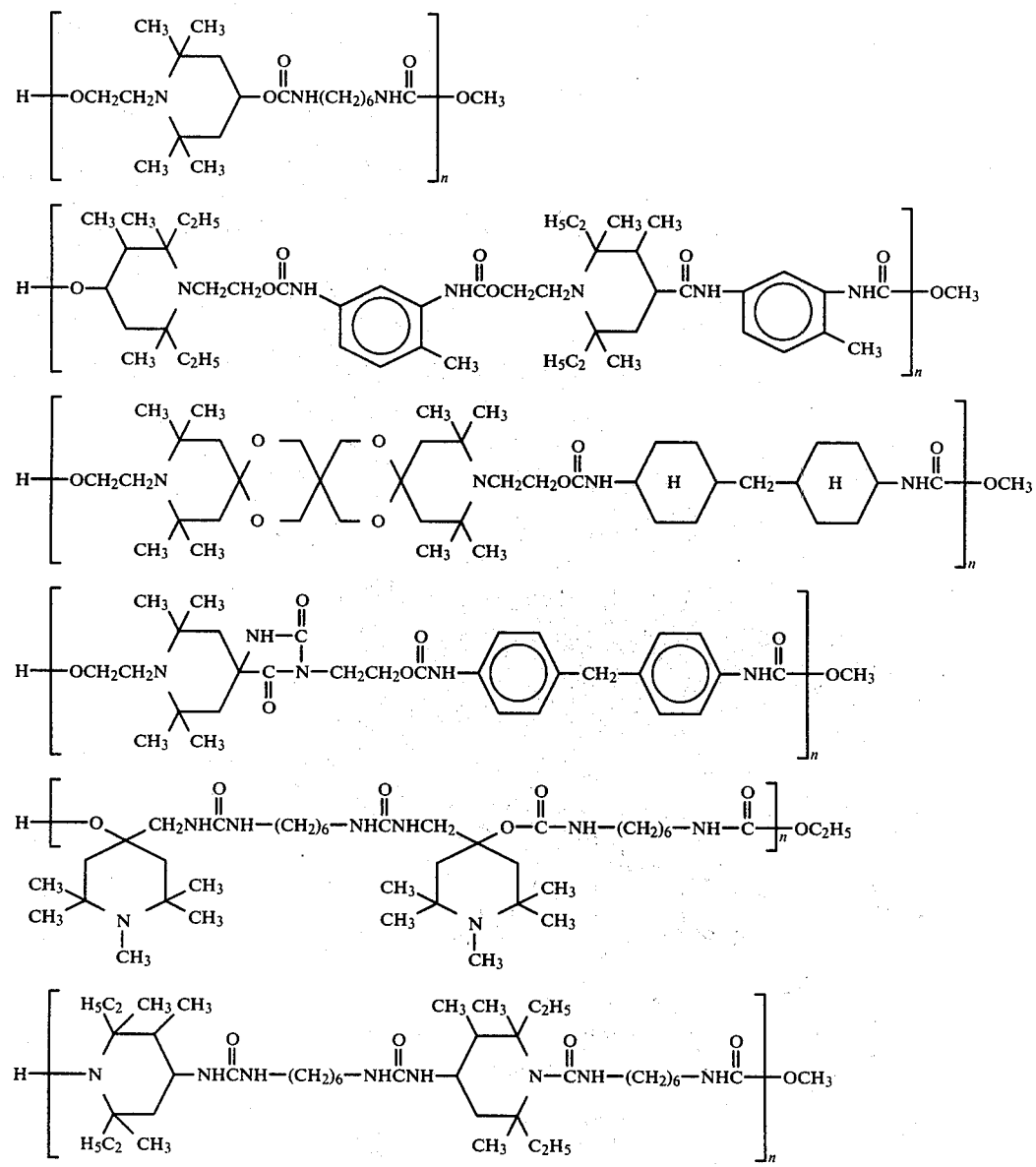

-continued
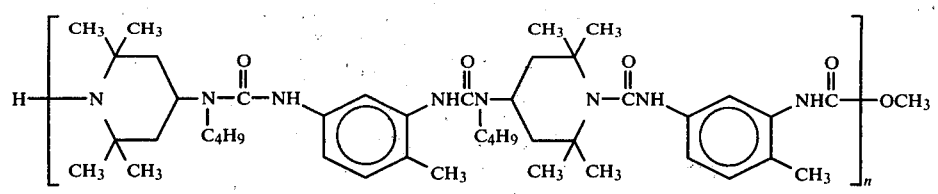
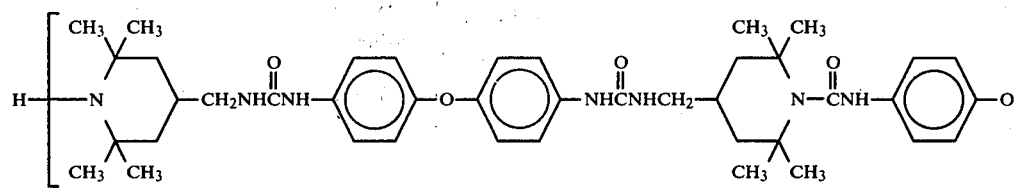
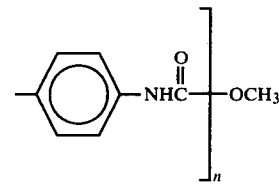
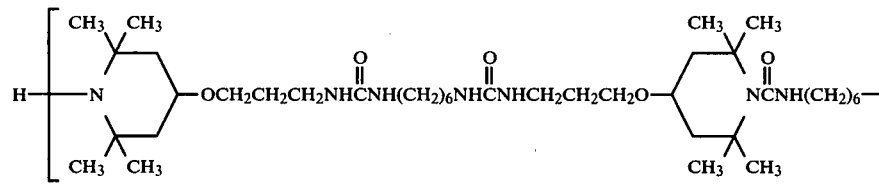
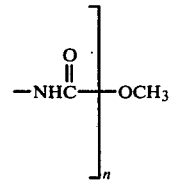
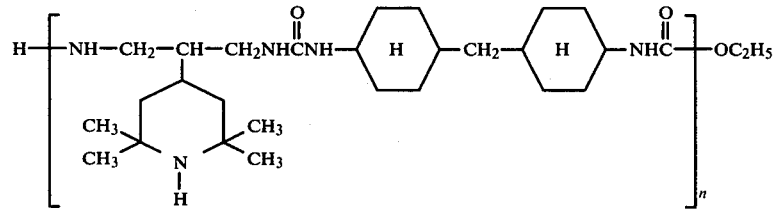
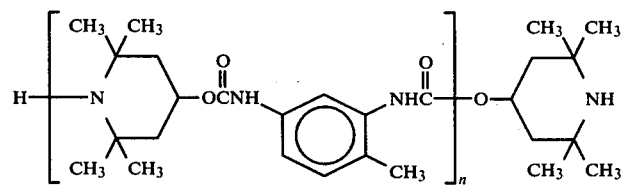
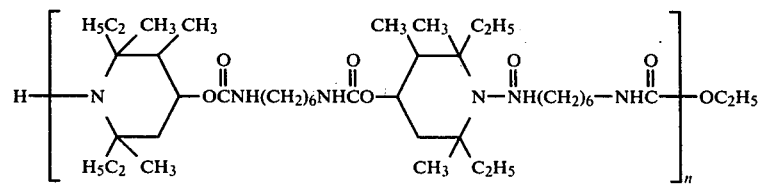

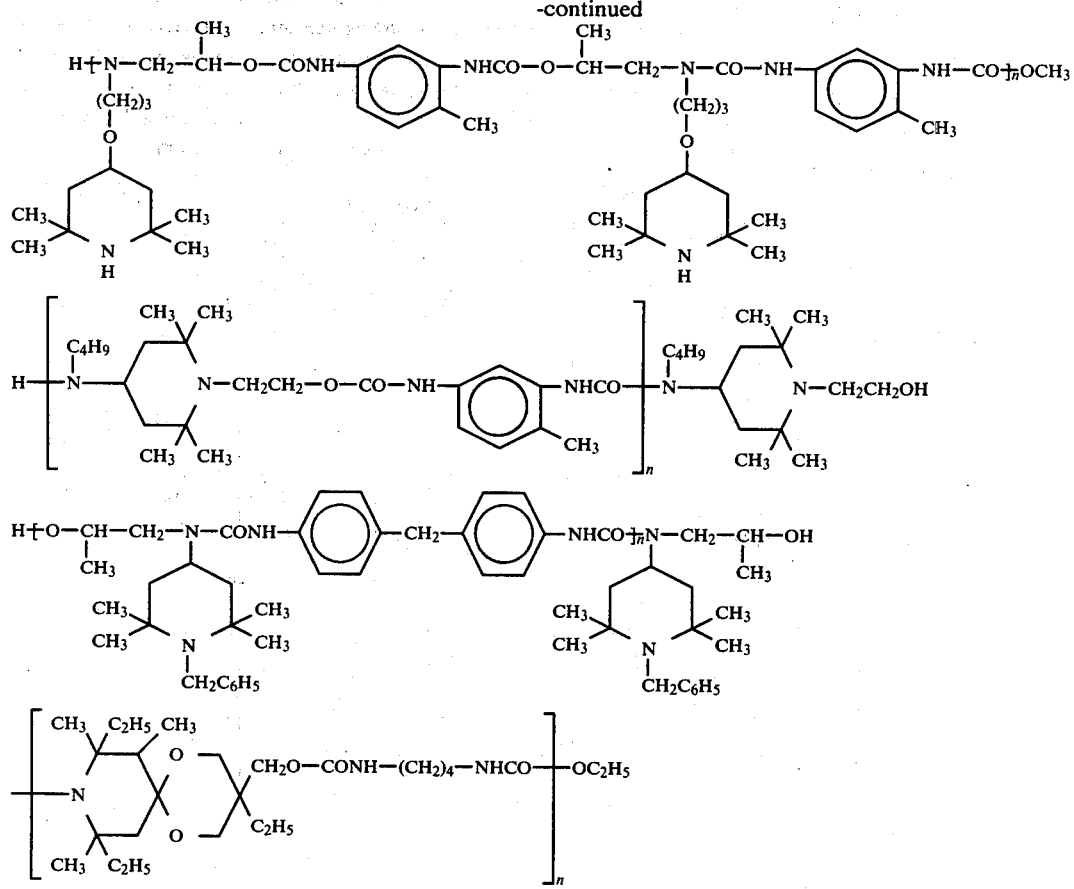
Sub-group 6
Polyesters of the formula II in which X is oxygen and —X—D—CO— represents one of the radicals of the formulae L to LIX.
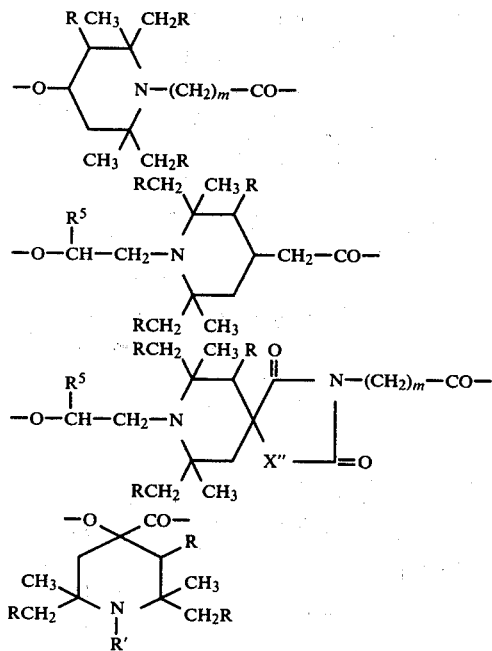

-continued

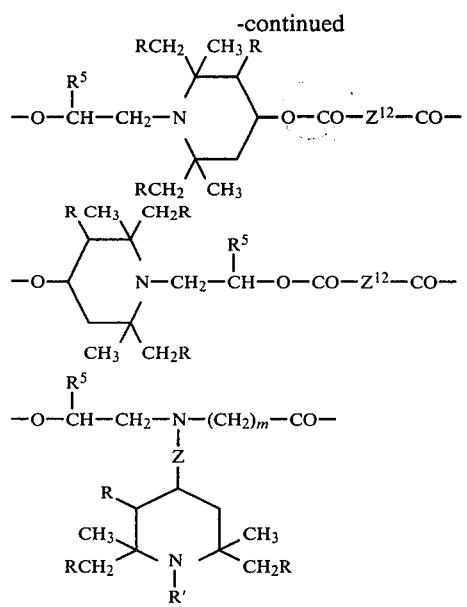

in which m, X", Z, R, R' and $Z^{12}$ have the same meaning as in sub-group 1 and $R^5$ has the same meaning as in sub-group 3.

Polyesters of this type are obtained by a polycondensation reaction of hydroxycarboxylic acids of the formula HO—D—COOH or lower alkyl esters thereof. Examples thereof are (a) 1-carboxyalkyl-4-hydroxy-polyalkyl-piperidines which can be prepared by carboxyalkylating 4-hydroxy-polyalkyl-piperidines.

(b) 1-Hydroxyalkyl-polyalkyl-piperidine-4-acetic acids which can be prepared from the corresponding NH compounds, described in DT-OS 2,337,865, by a reaction with ethylene oxide, propylene oxide or styrene oxide.

(c) Hydroxycarboxylic acids of the formula H—LII—OH and the alkyl esters thereof which can be prepared by a stepwise carboxyalkylation and hydroxyalkylation of the corresponding NH compounds.

(d) 4-Hydroxy-polyalkylpiperidine-4-carboxylic acids and esters thereof, such as are described in German Pat. Nos. 91,121 and 90,245.

(e) Hydroxycarboxylic acids of the formula H—LIV—OH, the alkyl esters of which can be obtained by reacting 4-hydroxyethyl-piperidines with chloroacetates, acrylates or 4-bromobutyrates.

(f) Hydroxycarboxylic acids of the formula H—LV—OH, the alkyl esters of which can be obtained by reacting the corresponding NH compounds as described under (e).

(g) Hydroxycarboxylic acids of the formula H—LVI—OH can be obtained by reacting the corresponding NH compounds with cyclic dicarboxylic acid anhydrides and their esters are formed from the NH compounds and dicarboxylic acid dialkyl esters.

(h) Hydroxycarboxylic acids of the formula H—LVII—OH and esters thereof can be obtained from the corresponding 4-hydroxy-piperidines by reaction with chloroacetates or acrylates or with butyrolactone.

(i) Hydroxycarboxylic acids H—LVIII—OH and H—(LVIIIa)—OH, such as can be prepared by reacting the corresponding hydroxy compounds with 1 mol of a cyclic dicarboxylic acid anhydride.

(k) Hydroxycarboxylic acids H—LIX—OH, such as can be prepared by stepwise carboxyalkylation and hydroxyalkylation of the corresponding primary amines.

Examples of polyesters of the formula II are:

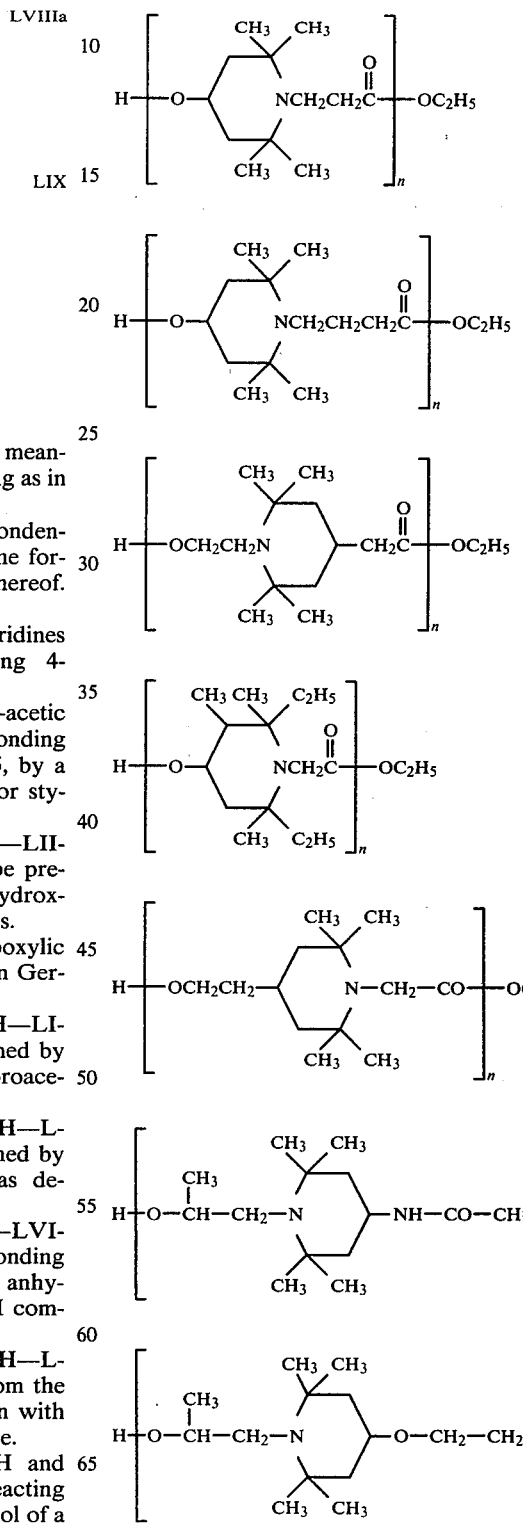

Sub-group 7

Polyamides of the formula II in which X is NH and —X—D—CO— represents a group of the formulae LX, LXI or LXII.

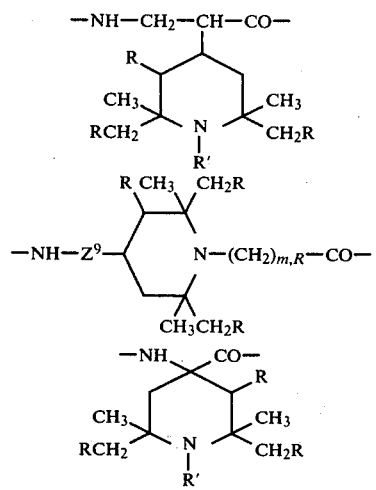

—NH—CH$_2$—CH—CO—   LX

—NH—Z$^9$—   N—(CH$_2$)$_{m,R}$—CO—   LXI

—NH   CO—   LXII in which m and R' have the same meaning as in sub-group 1 and Z$^9$ has the same meaning as in sub-group 5a.

Polyamides of this type are obtained by a polycondensation reaction of aminocarboxylic acids of the formula H$_2$N—D—COOH or esters thereof.

Aminocarboxylic acids of the formula H—LX—OH and esters thereof can be obtained by a condensation reaction of cyanoacetates with the corresponding 4-oxopiperidines and subsequent hydrogenation of the reaction products. Compounds of the formula H—LXI—OH and esters thereof, in which Z$^9$ is —CH$_2$CH$_2$—, can be obtained by carboxyalkylation of the polyalkyl-piperidinylene-4-acetonitriles described in DT-OS No. 2,352,379 and subsequent hydrogenation of the intermediate product. The corresponding compounds in which Z$^9$=—CH$_2$CH$_2$CH$_2$O— can be obtained from 4-hydroxy-polyalkylpiperidines by stepwise cyanoethylation, carboxyalkylation and hydrogenation.

Compounds of the formula H—LXII—OH are described in Bull. Soc. Chem. France 1967, 814.

Preferably, the lower alkyl esters of these aminocarboxylic acids are used.

Examples of polyamides of the formula II are given in the following formulae:

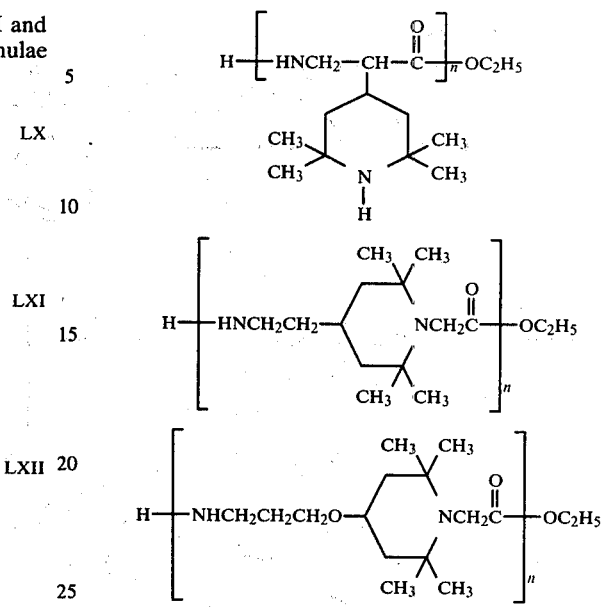

Sub-group 8

Polysilyl esters of the formula III in which R$^1$ and R$^2$ independently of one another denote methyl, ethyl or phenyl and E represents one of the radicals of the formulae XVIII to XXX, listed under 3). These polysilyl esters are prepared by a polycondensation reaction of difunctional silanes of the formula

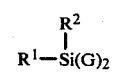

with diols of the formula HO—E—OH wherein G can denote chlorine, methoxy, ethoxy or phenoxy.

Examples of such difunctional silanes are: dimethyl-dichlorosilane, diphenyl-dichlorosilane, methyl-phenyl-dichlorosilane, methyl-ethyl-dichlorosilane, dimethyl-diethoxysilane and diphenyl-dimethoxysilane.

When dichlorosilanes are employed, the polycondensation reaction is preferably carried out in the presence of organic bases as HCl acceptors. Examples of these are triethylamine, tributylamine or pyridine.

The end groups of the low-polymeric polysilyl esters are preferably alcoholic hydroxyl groups and Si—OH or Si—Cl groups.

Examples of silyl esters of the formula III are given in the following formulae:

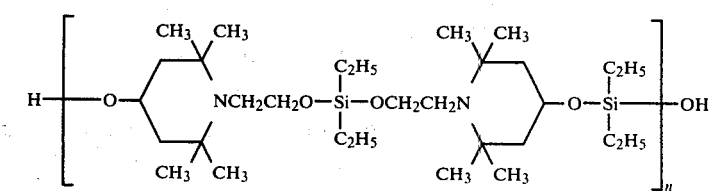

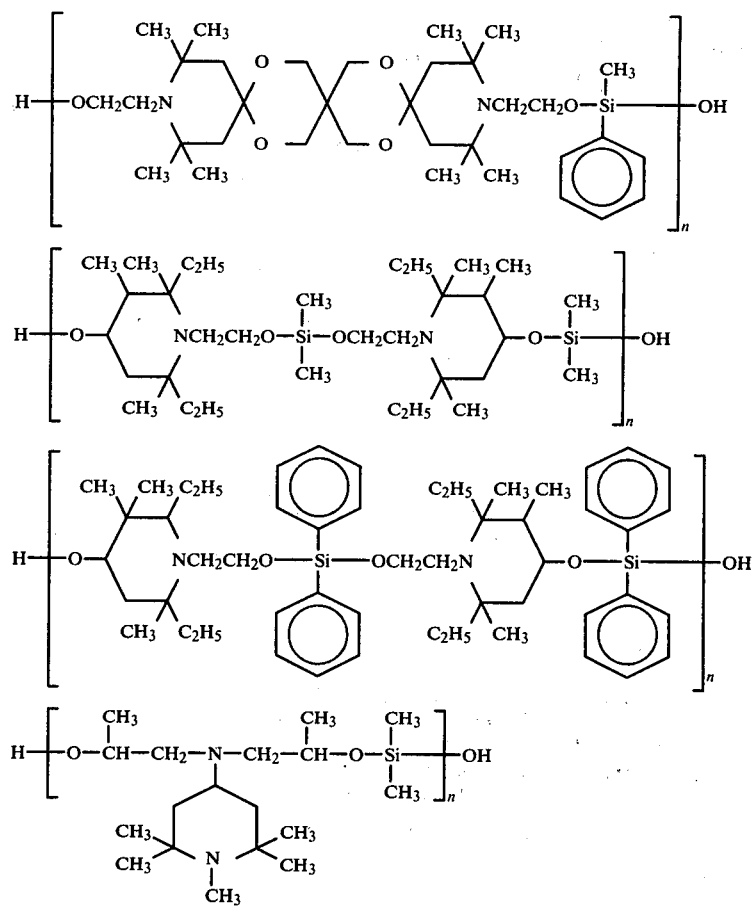

Sub-group 9

Polyethers of the general formula IV, in which A is a divalent radical of the formulae XVIII to XXX and F is alkylene with 2-12 C atoms, alkenylene with 4-8 C atoms, xylylene, hexahydroxylylene or one of the radicals

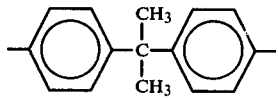

-CH$_2$-CH(OH)-CH$_2$-O-Z$^{10}$-O-CH$_2$-CH(OH)-CH$_2$- or -CH$_2$CH$_2$-O-CH$_2$CH$_2$-, in which Z$^{10}$ represents alkylene with 2-6 C atoms, -CH$_2$CH$_2$-O-CH$_2$CH$_2$-, cyclohexylene, phenylene or Polyethers of this type can be manufactured by reacting diols of the formulae HO-XVIII-OH to HO-XXX-OH with dihalides of the formula Hal-F-Hal (in which Hal can be chlorine, bromine or iodine), optionally with the addition of bases.

A second method of manufacture is the reaction of the said diols with epichlorohydrin with the addition of alkali, or with diglycidyl ethers in an approximate molar ratio of 1:1.

A third method of manufacture is the reaction of polyalkylpiperidine-containing diglycidyl ethers of the formula

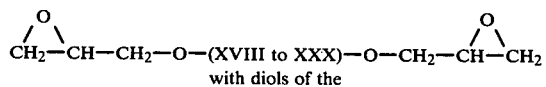

with diols of the formula HO—F—OH.

The formulae which follow give examples of such polyethers:

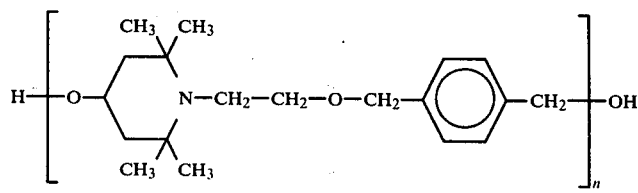

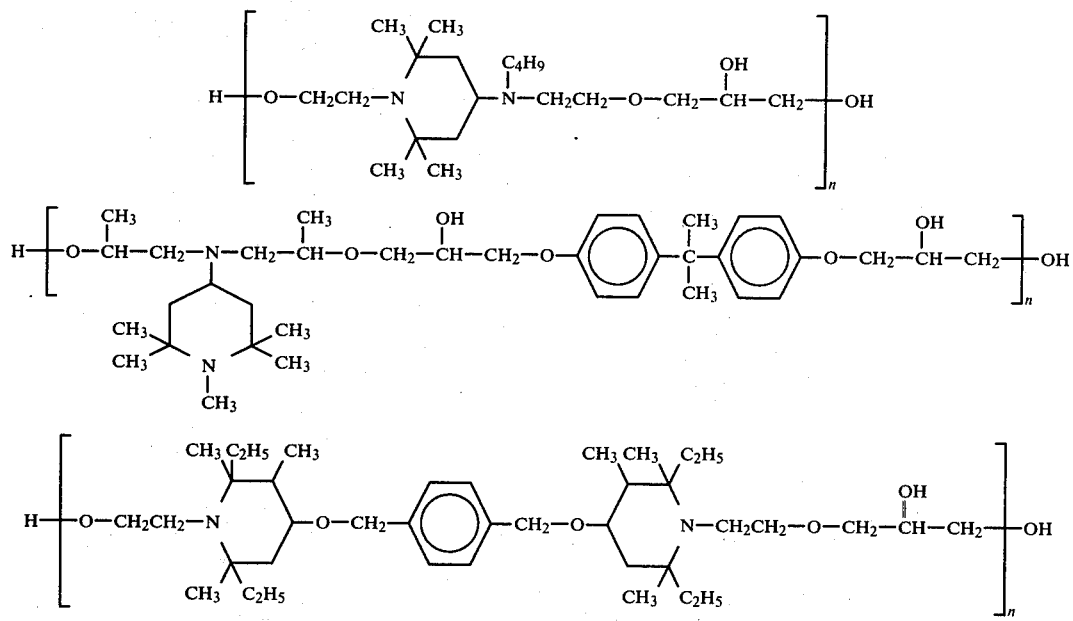

Sub-group 10

Polyethers of the general formula V, in which G is a radical of the formula LXIII or LXIV,

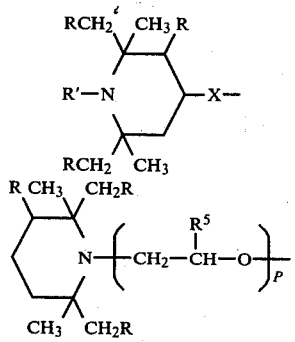

in which X is oxygen or NY, Y, R and R' have the meaning indicated for sub-group 1, R⁵ has the meaning indicated for sub-group 3 and p is nought or 1.

These polyethers are manufactured by polymerisation of monoepoxides of the formula

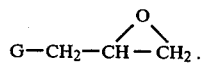

The polymerisation can be initiated by cationic or anionic catalysts, for example by boron fluoride or by lithium ethoxide. Examples of such polyethers can be given by the following formulae:

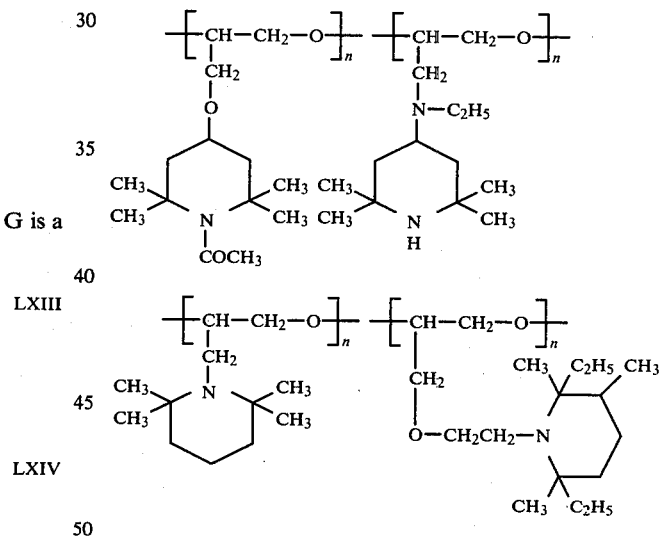

When piperidine-free monoepoxides, such as, for example, ethylene oxide, propylene oxide, butylene oxide, styrene oxide, cyclohexene oxide or phenyl glycidyl ether, are also used, copolymers are obtained and block copolymers are preferably formed.

Sub-group 11

Polyamines of the formula IVa, in which A represents a divalent radical of the formulae XXXI to XXXIX (of sub-group 4) which contains a polyalkylpiperidine radical and F has the same meaning as in sub-group 9. These polyamines can be manufactured from the diamines YNH—XXXI—NHY to YNH—XXXIX—NHY by reaction with dihalides Hal-F-Hal or with diepoxides or with epichlorohydrin.

Those polyamines of the formula IVa in which -NY-A-NY- represents a radical of the formula LXV or LXVI

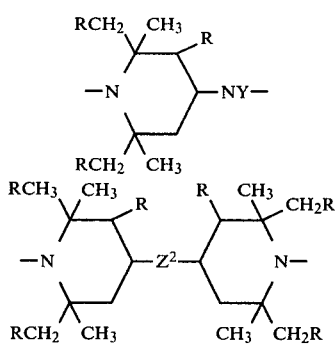

wherein R and $Z^2$ have the meaning given in sub-group 1, Y has the meaning given in sub-group 2 and F has the meaning given above, can be manufactured analogously.

Sub-group 11a

Polyamines of the formula IVa, in which A represents a radical of the formula $-CH_2-CH(OH)-CH_2-Z^{11}-CH_2-CH(OH)-CH_2-$ and $Z^{11}$ represents a radical of the formula LXVII to LXX

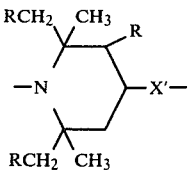

in which R, R', B' and Z have the meaning given for sub-group 1 and $Z^5$ has the meaning given for sub-group 3 and denotes X'—O— or —NY— and Y has the meaning given for sub-group 2, and in which F has the same meaning as B in sub-group 2, can be manufactured by a polyaddition reaction of the diepoxides

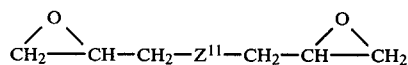

with diamines of the formula YNH—F—NHY.

The diepoxides can be manufactured by reacting the compounds H—LXV—H to H—LXX—H with at least 2 mols of epichlorohydrin and 2 mols of alkali.

Examples of polyamines of sub-group 11 and 11a are the following compounds:

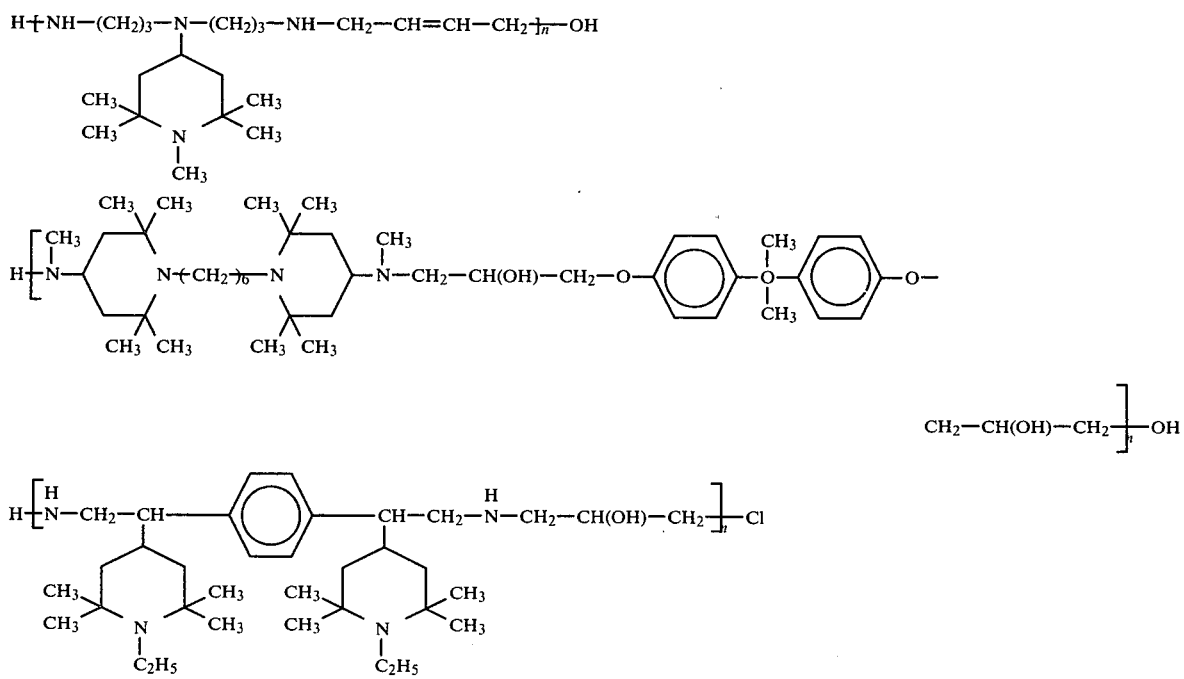

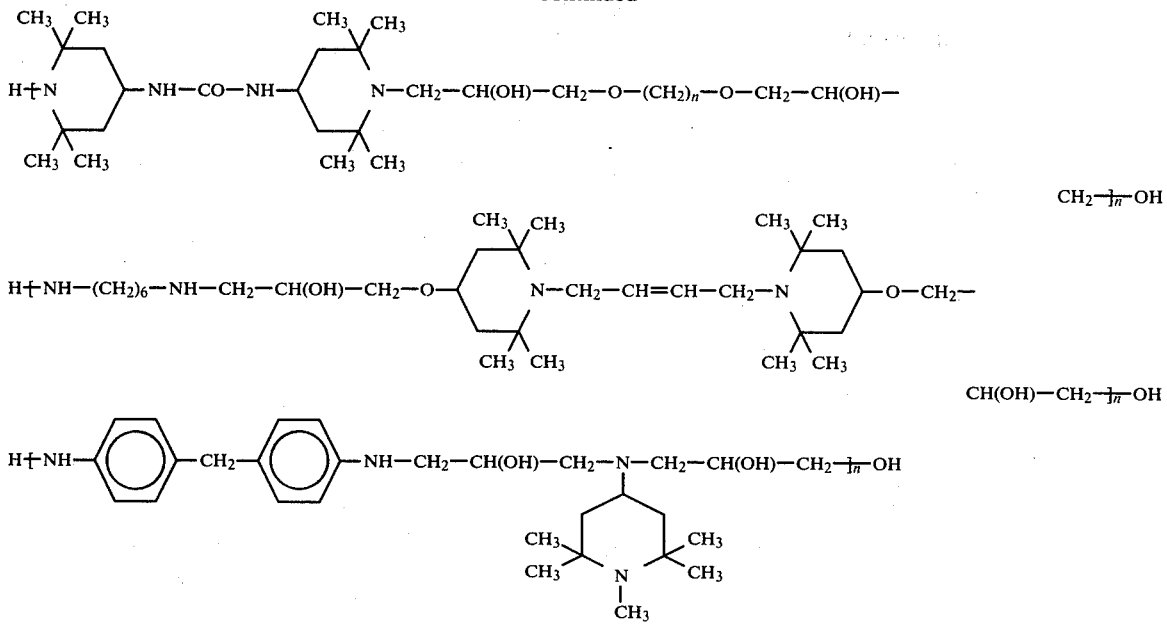

Sub-group 12

Polyamines of the formula VII, in which G represents a radical of the formula VIII and F has the same meaning as in sub-group 9 or is a radical of the formula —CH$_2$—CH(OH)—CH$_2$—Z$^{11}$—CH$_2$—CH(OH)-CH$_2$-.

Polyamines of this type can be manufactured from the primary amines VIII-NH$_2$ by reaction with a dihalide Hal-F-Hal, with a diepoxide of the formula

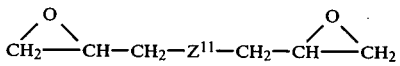

or a diglycidyl ether

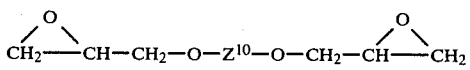

or with epichlorohydrin in the presence of alkali.

In these formulae Z$^{10}$ has the same meaning as in sub-group 9 and Z$^{11}$ has the same meaning as in sub-group 11a.

Copolyamines of sub-group 12 can be obtained by the additional use of piperidine-free primary amines, such as, for example, butylamine, dodecylamine, aniline or cyclohexylamine.

Sub-group 12a

Polyamines of the formula VII, in which G denotes alkyl with 1–18 C atoms, cycloalkyl with 5–12 C atoms, aralkyl with 7–12 C atoms or aryl or alkaryl with 6 to 16 C atoms and F represents a radical —CH$_2$—CH(OH)—CH$_2$—Z$^{11}$—CH$_2$—CH(OH)—CH$_2$—. These polyamines can be manufactured by reacting primary amines of the formula G—NH$_2$ with the bis-epoxides

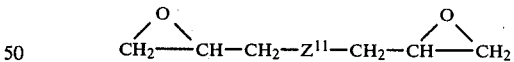

Examples of polyamines of sub-group 12 and 12a are shown by the following formulae:

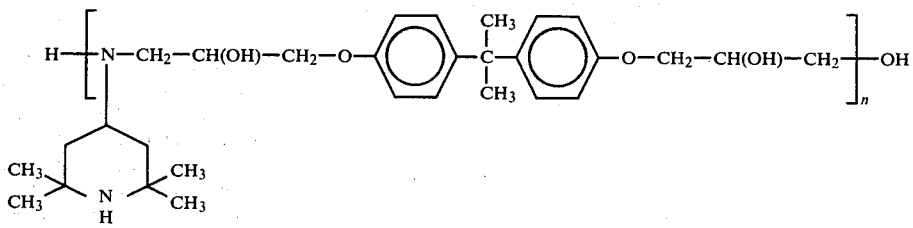

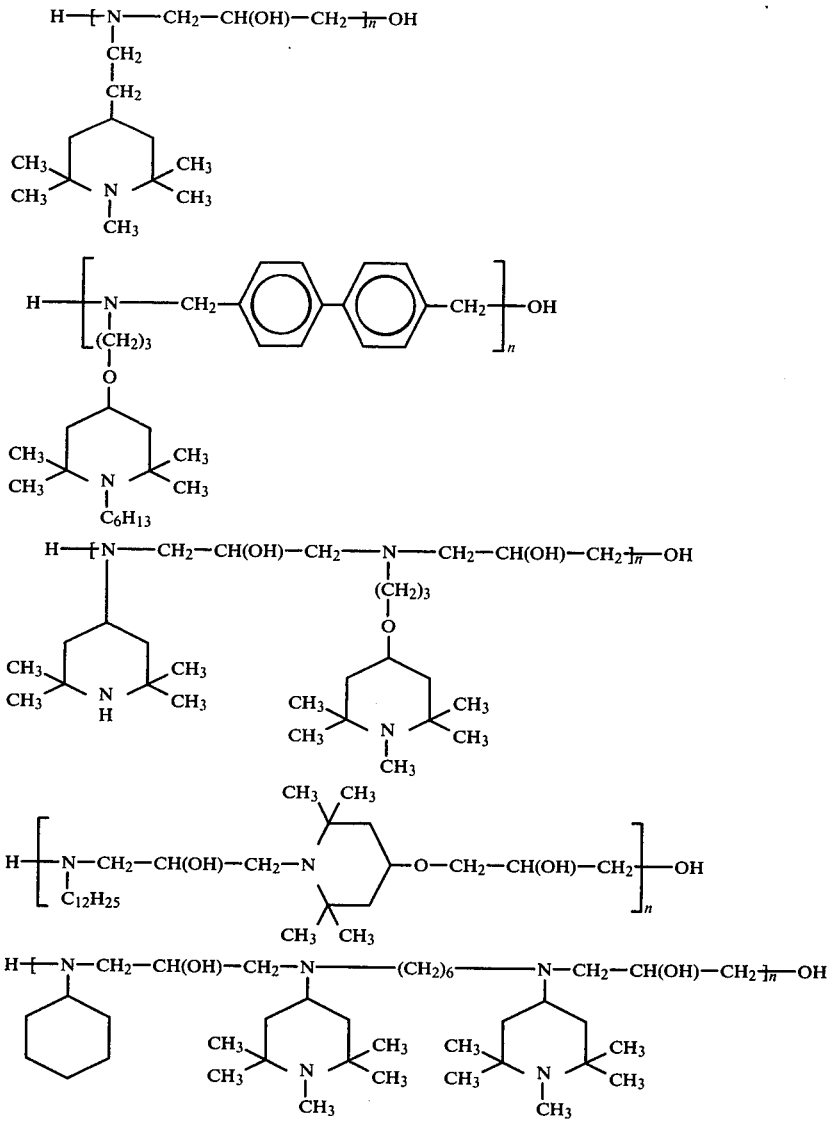

Sub-group 13

Polycarbonates of the general formula VI, in which X is oxygen and A represents a divalent radical of the formulae XVIII to XXX.

Polycarbonates of this type can be manufactured by reacting the diol HO—XVIII—OH to HO—XXX—OH with phosgene or a carbonic acid ester.

The polyalkylpiperidine radical can be in the main chain or in the side chain, as is shown by the two examples which follow:

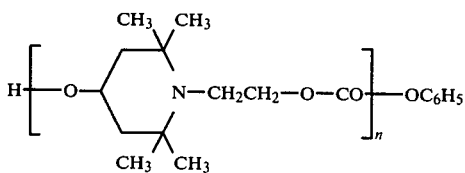

-continued

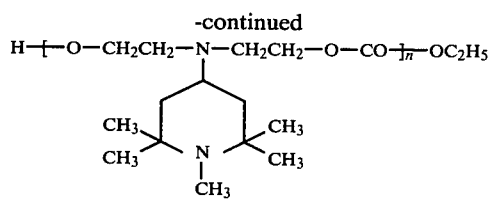

Copolymers of sub-group 13 can be obtained by the additional use of piperidine-free diols, preferably bisphenols.

Sub-group 14

Polyureas of the general formula VI, in which X is —NY— and either A has the same meaning as B in sub-group 4 and Y has the meaning given in sub-group 2 or A has the same meaning as B in sub-group 2 and Y has the meaning given in sub-group 2.

Polyureas of this type can be manufactured from diamines of the formula HNY—A—NYH by reaction with carbonic acid esters or phosgene or urea. The polyalkylpiperidine radical can be present in radical A or in radical Y or in both radicals.

Examples of such polyureas are:

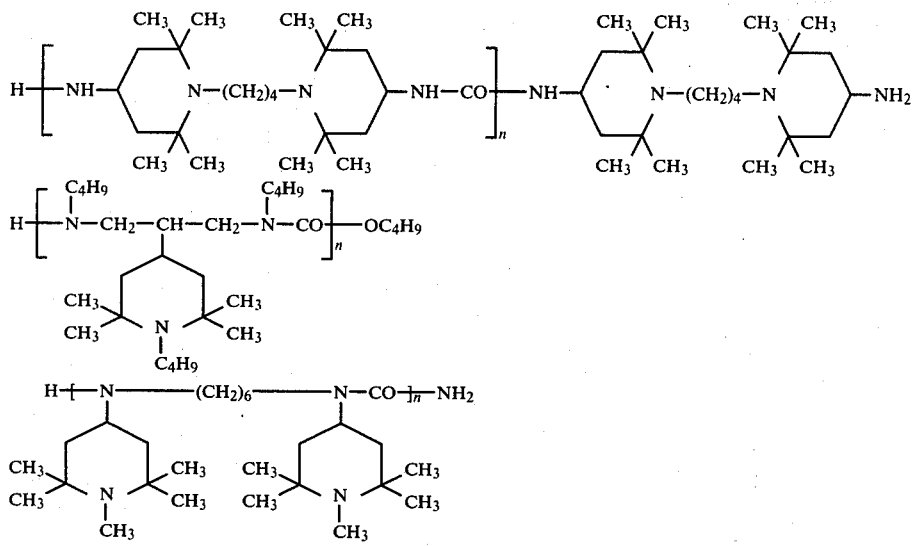

All the monomeric polyalkylpiperidine derivatives used for preparing the compounds of the sub-groups 1–14 are by themselves active as light stabilisers for organic materials.

Amongst the compounds, according to the invention, of the formulae I to VII, those compounds are preferred in which R denotes methyl or, especially, hydrogen, since these polyalkylpiperidine derivatives are most readily acceptable.

Because of the ready accessibility of the starting components and because of their outstanding light stabilising action, the following are particularly preferred:

(a) Polyesters of the formula I in which X and X' are oxygen, B has the meaning given in sub-group 1 and A denotes one of the radicals of the formulae XIV, XV or XVI, in which R and R' denote hydrogen or methyl, Z is a direct bond, m is 1 or 2 and $Z^1$, $Z^2$ and B' have the meaning given in sub-group 1.

(b) Polyamides of the formula I in which X and X' denote NH, B has the meaning given in sub-group 2 and A represents one of the radicals XIV, XV or XVI, in which R and R' denote hydrogen or methyl, Z is a direct bond and m, $Z^1$, $Z^2$ and B' have the meaning given in sub-group 1.

(c) Polyesters of the formula I in which X and X' are oxygen, A denotes alkylene or a phenyl-substituted or benzyl-substituted alkylene with 1–15 C atoms or arylene with 6–12 C atoms and B represents one of the radicals of the formulae XVIII, XXI, XXV or XXX, in which R, R' and $R^5$ are hydrogen or methyl and B"$Z^2$, $Z^5$ and $Z^6$ have the meaning given in sub-group 3.

(d) Polyesters of the formula II in which —X—D—CO— represents a radical of the formula L, LV, LVI or LVII, in which R, $R^3$ and $R^5$ are hydrogen or methyl, m is 1 or 2, Z denotes a direct bond and $Z^{12}$ represents 1,2-ethylene, 1,3-propylene, vinylene or o-phenylene.

(e) Polyamides of the formula I in which X and X' are NH, A represents alkylene with 1–12 C atoms or arylene with 6–12 C atoms and B represents a radical of the formula XXXVI or XXXVIII in which R and R' are hydrogen or methyl, Z represents a direct bond and $Z^5$ is alkylene or alkenylene with 4–8 C atoms or p-xylylene.

(f) Polyamides of the formula I in which X is NY and X' is NH or NY, Y is a tetramethylpiperidine radical of the formula XLa $$\text{XLa}$$

A denotes alkylene with 1–12 C atoms or arylene with 6–12 C atoms and B denotes alkylene with 2–12 C atoms, arylene with 6–12 C atoms, 4,4'-dicyclohexylene-methane or phenylene-$Z^4$-phenylene in which $Z^4$ represents —CH$_2$—, >C(CH$_3$)$_2$, —O— or —SO$_2$—

(g) Polyethers of the formula IV in which F has the same meaning as in sub-group 9 and A represents one of the radicals XVIII, XXI, XXV or XXX, in which R, R' and $R^5$ are hydrogen or methyl and $Z^2$, $Z^5$, $Z^6$ and B" has the meaning indicated in subgroup 3.

(h) Polyethers of the formula V, in which G is a radical of the formula LXIV, in which R denotes hydrogen and p denotes nought.

(i) Polyamines of the formula VII in which G represents a 2,2,6,6-tetramethylpiperidin-4-yl radical and F has the meaning indicated in sub-group 9.

According to the invention, the compounds of the general formulae I to VII can be used as light stabilisers for plastics and, in this use, they are distinguished by high resistance to extraction. Examples of polymeric substrates which can be stabilised in this way against light degradation are the following:

1. Polymers of monoolefines and diolefines, for example polyethylene (which optionally can be crosslinked), polypropylene, polyisobutylene, polymethylbutene-1, polymethylpentene-1, polyisoprene or polybutadiene.

2. Mixtures of the polymers mentioned under (1), for example mixtures of polypropylene with polyethylene or with polyisobutylene.

3. Copolymers of monoolefines and diolefines, such as, for example, ethylene/propylene copolymers, propylene/butene-1 copolymers, propylene/isobutylene copolymers, ethylene/butene-1 copolymers and terpolymers of ethylene with propylene and a diene, such as hexadiene, dicyclopentadiene or ethylidenenorbornene.

4. Polystyrene.

5. Copolymers of styrene or α-methylstyrene with dienes or acrylic derivatives, such as, for example, styrene/butadiene, styrene/acrylonitrile, styrene/acrylonitrile/methyl acrylate; mixtures of high impact strength from styrene copolymers and another polymer, such as, for example, a polyacrylate, a diene polymer or an ethylene/propylene/diene terpolymer; and block copolymers of styrene, such as, for example, styrene/butadiene/styrene, styrene/isoprene/styrene or styrene/ethylene/butylene/styrene.

6. Graft copolymers of styrene, such as, for example, styrene on polybutadiene, styrene and acrylonitrile on polybutadiene, and mixtures thereof with the copolymers mentioned under (5), such as are known as the so-called ABS polymers.

7. Halogen-containing polymers, such as, for example, polyvinyl chloride, polyvinylidene chloride, polyvinyl fluoride, polychloroprene, chlorinated rubbers and copolymers, such as vinyl chloride/vinylidene chloride, vinyl chloride/vinyl acetate.

8. Polymers which are derived from α,β-unsaturated acids and derivatives thereof, such as polyacrylates and polymethacrylates, polyacrylamides and polyacrylonitrile.

9. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate, polyallylmelamine and copolymers thereof with other vinyl compounds, such as ethylene/vinyl acetate copolymers.

10. Homopolymers and copolymers of epoxides, such as polyethylene oxide, polypropylene oxide or copolymers thereof with bis-glycidyl ethers.

11. Polyacetals, such as polyoxymethylene and those polyoxymethylenes which contain ethylene oxide as a comonomer.

12. Polyphenylene oxides.

13. Polyurethanes and polyureas.

14. Polycarbonates.

15. Polysulphones.

16. Polyamides and copolyamides which are derived from diamines and dicarboxylic acids and/or from aminocarboxylic acids or the corresponding lactams, such as polyamide 6, polyamide 6/6, polyamide 6/10, polyamide 11 and polyamide 12.

17. Polyesters which are derived from dicarboxylic acids and dialcohols and/or from hydroxycarboxylic acids or the corresponding lactones, such as polyethylene terephthalate, polybutylene terephthalate and poly-1,4-dimethylol-cyclohexane terephthalate.

18. Crosslinked polymers which are derived from aldehydes on the one hand and phenols, ureas and melamines on the other hand, such as phenol/formaldehyde resins, urea/formaldehyde resins and melamine/formaldehyde resins.

19. Alkyd resins, such as glycerol/phthalic acid resins and mixtures thereof with melamine/formaldehyde resins.

20. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

21. Crosslinked epoxide resins which are derived from polyepoxides, for example from bis-glycidyl ethers or from cycloaliphatic diepoxides.

22. Natural polymers, such as cellulose, rubber, proteins and derivatives thereof which are chemically modified in a polymer-homologous manner, such as cellulose acetates, cellulose propionates and cellulose butyrates, or the cellulose ethers, such as methylcellulose.

Amongst these polymers, the groups 1–6, 13, 16 and 17 should be singled out since the stabilisers according to the invention have a particularly marked effect in these substrates.

The stabilisers are incorporated in the substrates in a concentration from 0.005 to 5% by weight, calculated on the material to be stabilised.

Preferably, 0.01 to 1.0, particularly preferentially 0.02 to 0.5, % by weight of the compounds, calculated on the material to be stabilised, are incorporated in the latter. The incorporation can be effected, for example, by admixing at least one of the compounds of the formulae I to VII and optionally further additives by the methods customary in industry, before or during shaping, or by applying the dissolved or dispersed compounds to the polymer, if appropriate, with subsequent evaporation of the solvent.

The plastics stabilised in this way can, in addition, also contain further stabilisers or other additives customary in plastics technology, such as are listed, for example, in DT-OS No. 2,349,962, page 25–32.

When known stabilisers are used in addition, synergistic effects can arise, and this is frequently the case especially when other light stabilisers or organic phosphites are used in addition.

The additional use of antioxidants in the stabilisation of polyolefines is particularly important.

The examples which follow explain the invention in further detail, without limiting it. In the examples, parts are to be understood as parts by weight and percentages are to be understood as percent by weight; the temperatures are given in degrees centigrade.

EXAMPLE 1

80.4 g (0.4 mol) of 1-(2-hydroxyethyl)-2,2,6,6-tetramethyl-4-hydroxypiperidine are warmed to 100° under nitrogen with 58.4 g (0.4 mol) of dimethyl succinate in 100 ml of xylene. After 2 g of sodium methylate has been added, the reaction mixture is held at 100° for 4 hours, methanol being slowly distilled off. After this period, the temperature of the mixture is slowly raised to 130°–35° and then stirred at this temperture for a further 6 hours. The amount of methanol distilled off is 24 g. The reaction mixture is diluted with 200 ml of toluene and the resulting solution is washed with three times 50 ml of water and dried over sodium sulphate. The brownish solution is then decolorised with 6 g of fullers earth (Tonsil AC) and evaporated in vacuo. The yellowish residue is dried at 120° in a high vacuum (0.1 mm Hg) for 15 hours. The resulting polyester is a viscous, yellowish resin (Compound No. 1), and a cryoscopic determination of the molecular weight gave an average molecular weight of about 2,000.

If an identical batch is warmed, after the addition of 2 g of lithium amide, to 130°–35° for 5 hours and then to 140°–45° for a further 7 hours, this gives, after identical working up, a polyester as a hard, slightly yellowish resin (Compound No. 2) which can readily be powdered and has a softening temperature of about 120°. A viscometric determination of the molecular weight gave an average molecular weight of about 4,000.

EXAMPLE 2

If 1-(2-hydroxyethyl)-2,2,6,6-tetramethyl-4-hydroxypiperidine and an equimolar amount of dimethyl adipate are used as the starting materials and the procedure followed is otherwise as described for Compound No. 1, this gives a polyester in the form of a thick viscous, slightly yellowish resin (Compound No. 3). A determination of the molecular weight (by cyroscopy) gave an average molecular weight of about 1,050.

EXAMPLE 3

When 1-(2-hydroxyethyl)-2,2,6,6-tetramethyl-4-hydroxypiperidine is reacted with an equimolar amount of dimethyl sebacate this gives, the procedure followed being as described for Compound No. 1, a polyester as an almost solid, yellowish resin (Compound No. 4) having an average molecular weight of about 1,750 (by cryoscopy).

EXAMPLE 4

When 1 (2-hydroxyethyl)-2,2,6,6-tetramethyl-4-hydroxypiperidine is made to react, as described for Compound No. 1, with dimethyl isophthalate, this gives a polyester in the form of a yellowish-brown resin (Compound No. 5) which can be powdered and has an average molecular weight of about 1,100 (by cryoscopy).

EXAMPLE 5

When 1-(2-hydroxyethyl)-2,2,6,6-tetramethyl-4-hydroxypiperidine is reacted, as described for Compound No. 1, with diethyl diethylmalonate, this gives a polyester as an almost colourless resin (Compound No. 6) which can readily be powdered and has an average molecular weight (by cryoscopy) of about 2,100.

EXAMPLE 6

If 1-(2-hydroxyethyl)-2,2,6,6-tetramethyl-4-hydroxypiperidine and an equimolar amount of diethyl dibutylmalonate are used as the starting materials and the procedure followed is otherwise as described for Compound No. 1, this gives a polyester in the form of a viscous, yellowish resin (Compound No. 7) with an average molecular weight of about 1,300 (by cryoscopy).

EXAMPLE 7

49.9 g (0.1 mol) of 1-(2-hydroxyethyl)-2,2,6,6-tetramethylpiperidine-4-spiro-2'-(1',3'-dioxane)-5'-spiro-5''-(1'',3''-dioxane)-2''-spiro-4'''-(1'''-(2-hydroxyethyl)-2''',2''',6''',6'''-tetramethylpiperidine are warmed to 100° under nitrogen with 25.8 g (0.1 mol) of diethyl sebacate in 100 ml of xylene. After 2 g of lithium amide have been added, the reaction mixture is stirred at 130°–35° for about 6 hours, ethanol being distilled off continuously (total amount of ethanol in the distillate about 9 g). The reaction mixture is worked up as indicated under Example 1. The polyester (Compound No. 8) obtained after drying in a high vacuum (18 hours at 120° under 0.1 mm Hg) is at room temperature a slightly yellowish, glassy mass which can be comminuted to give a colourless powder. A cryoscopic determination of the molecular weight gave an average molecular weight of 1,940.

EXAMPLE 8

If 1-(2-hydroxyethyl)-2,2,6,6-tetramethylpiperidine-4-spiro-2'-(1',3'-dioxane)-5'-spiro-5''-(1'',3''-dioxane)-2''-spiro-4'''-(1'''-(2-hydroxyethyl)-2''',2''',6''',6''40 -tetramethylpiperidine) and an equimolar amount of diethyl adipate are used as the starting materials and the reaction mixture is warmed to 130° for 4 hours as described above, this gives a polyester (Compound No. 9) which can be comminuted at room temperature to give a colourless powder and has an average molecular weight (by cryoscopy) of about 2,200.

EXAMPLE 9

20.1 g (0.1 mol) of 1-(2-hydroxyethyl)-2,2,6,6-tetramethyl)-4-hydroxypiperidine are warmed to 60° with 25 g of triethylamine in 400 ml of absolute dioxane. At this temperature, a solution of 25.3 g (0.1 mol) of diphenyldichlorosilane in 50 ml of absolute dioxane is added dropwise to the above solution in the course of about 4 hours. Subsequently, the reaction mixture is stirred further at 60°–65° for about 6 hours. After cooling to room temperature, the triethylamine hydrochloride which has separated out is filtered off and the solution is evaporated in vacuo. The residue is taken up in 200 ml of toluene and 50 ml of hexane are added to the toluene solution. A white flocculent precipitate forms immediately and is filtered off. The toluene/hexane solution is evaporated in vacuo and the residue is dried at 120° under 0.1 mm Hg for 15 hours. The resulting polysilyl ester (Compound No. 10) is a thick viscous, yellowish resin. A determination of the molecular weight gave an average molecular weight of about 2,000.

If, in place of diphenyldichlorosilane, 12.9 g of dimethyldichlorosilane are used and the procedure followed is otherwise as described above, this gives a polysilyl ester (Compound No. 11) as a thick, yellowish resin with an average molecular weight of about 1,400.

EXAMPLE 10

22.9 g (0.1 mol) of 1-methoxycabonylmethyl-2,2,6,6-tetramethyl-4-hydroxypiperidine in 100 ml of xylene are heated to 135° in a stream of nitrogen for 5 hours with 0.5 g of sodium methylate. During this period, a mixture of xylene/methanol slowly distils out of the reaction flask. Subsequently, the contents of the flask are kept at 100° under a vacuum of 12 mm Hg for 1 further hour. The contents of the flask are taken up in 100 ml of benzene with gentle warming and the mixture is neutralised with 0.6 g of acetic acid and left to stand at room temperature for about 1 hour. 200 ml of hexane are then added slowly to the clarified benzene solution. A fine pulverluent precipitate is formed, and this is filtered off and dried at 50° under 0.1 mm Hg for 18 hours. The resulting polyester (Compound No. 12) is a colourless powder with a softening point of about 110° and an average molecular weight (by viscometry) of about 1,400.

EXAMPLE 11

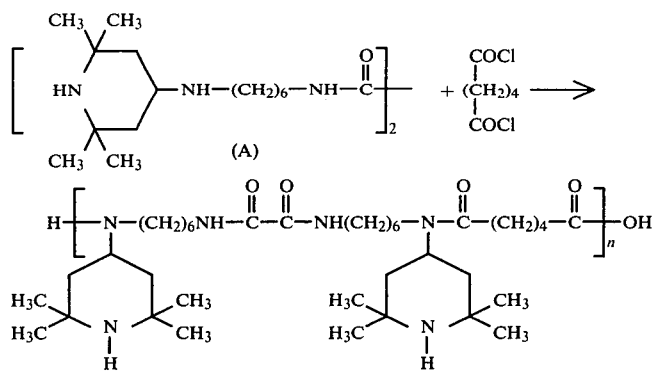

56.4 g of compound A are initially introduced into 500 ml of chloroform at room temperature. A solution of 18.3 g of adipic acid chloride dissolved in 50 ml of chloroform is added dropwise to this mixture in the course of about 2 hours. The mixture is then stirred exhaustively for 3 hours at room temperature and for 1 hour at 50°. After cooling to room temperature, 300 ml of 10% strength sodium hydroxide solution are added to the viscous chloroform solution and the mixture is stirred intensively for 3 hours. The aqueous phase is separated off and the chloroform solution is now poured slowly into 2 l of hexane, whilst stirring well. The polymer, which separates out as a colourless resin, is separated from the solvent, taken up in 300 ml of chloroform and precipitated again with hexane. The resin which separates out is dried for 24 hours at 60° under a high vacuum (0.1 mm). The resulting polyamide (Compound No. 13) is a resin which can be powdered and has a sintering point of about 92°, an average molecular weight of about 6,100 and a water content of 2.4%.

Compond A is obtained from triacetonamine and hexamethylenediamine (ratio 1:1) by hydrogenative amination and subsequent amidation with diethyl oxalate (melting point 89°–90°).

EXAMPLE 12

During the entire reaction time, the methanol formed is distilled off as a mixture with a little xylene. The viscous solution is diluted with 100 ml of xylene and poured into 2 l of hexane. The resin which separates out is dissolved in 300 ml of toluene and precipitated again using hexane and then dried for 24 hours at 80° under a high vacuum (0.1 mm). After cooling, a resin which can be comminuted to give a slightly yellowish powder is obtained. The resulting polyester-polyamide (Compound No. 14) sinters at about 135° and has a molecular weight (vapour pressure method) of about 3,600.

EXAMPLE 13

79 g of 1,6-bis-(2,2,6,6-tetramethyl-4-piperidylamino)-hexane are dissolved in 400 ml of chloroform. A solution of 36.6 g of adipic acid chloride in 50 ml of chloroform is added dropwise to this solution at room temperature in the course of about 90 minutes. The reaction mixture is stirred exhaustively for 15 hours at room temperature and then for 2 hours at 50°. After cooling to room temperature, 300 ml of 2 N sodium hydroxide solution are added to the reaction solution and the mixture is stirred intensively for 4 hours. The aqueous phase is separated off and the chloroform solution is washed with twice 300 ml of water and then poured into 2 l of hexane. The resin which separates out is dissolved in 300 ml of chloroform and again precipi-

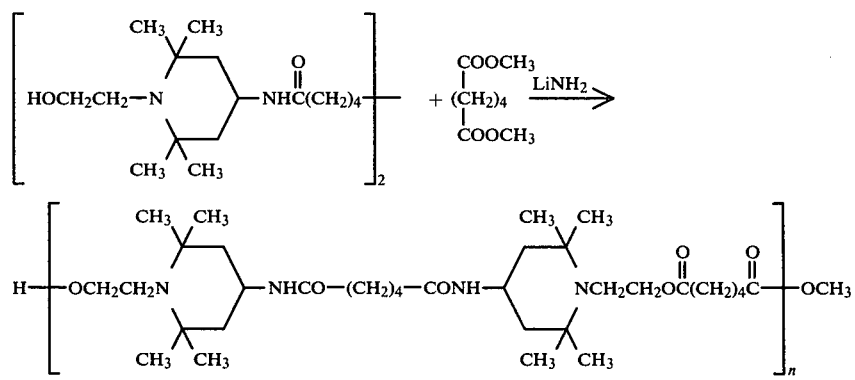

42.5 g of N,N'-bis-[1-(2-hydroxyethyl)-2,2,6,6-tetramethyl-4-piperidyl]-sebacamide (melting point 182°–83°, prepared from N,N'-bis-(2,2,6,6-tetramethyl-4-piperidyl)-sebacamide and 2 mols of ethylene oxide) are warmed with 13.0 g of dimethyl adipate and 0.5 g of lithium amide in 100 ml of xylene, first to 100° for 2 hours, then to 120° for 2 hours and subsequently to 140° for a further 18 hours, under a gentle stream of nitrogen.

tated using hexane. The resulting polyamide (compound No. 15) is dried for 24 hours at 60°/0.1 mm. It can be ground to a virtually colourless powder which sinters at about 140° and has an average molecular weight of about 4,500.

A polyamide (compound No. 16) which has an average molecular weight of about 1,500 and sinters at about 40° can be isolated from the hexane/chloroform solution by evaporation.

EXAMPLE 14

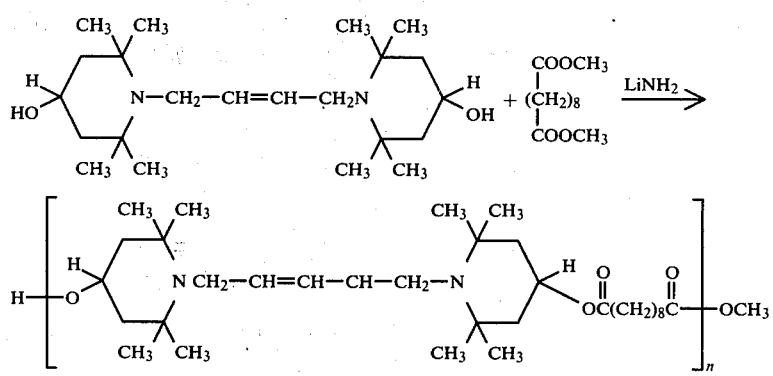

36.6 g of 1,4-bis-(4-hydroxy-2,2,6,6-tetramethyl-piperidin-1-yl)-but-2-ene are warmed with 23.0 g of dimethyl sebacate and 80 mg of lithium amide in 300 ml of xylene to 140° for 8 hours, under a gentle stream of nitrogen. During the entire reaction time, the methanol formed is distilled off as a mixture with the xylene. The viscous residue is dissolved in 50 ml of chloroform and the solution is poured warm into 700 ml of methanol. After stirring intensively for about 20 minutes, the polyester forms a pulverulent suspension which can be filtered easily and this suspension is filtered and the polyester is washed with methanol and dried for 24 hours at 80° under a high vacuum (0.1 mm). The resulting polyester (compound No. 17) sinters at about 105° and has an average molecular weight (vapour pressure method, of about 5,000.

The reaction of 1,4-bis-(4-hydroxy-2,2,6,6-tetramethylpiperidin-1-yl)-but-2-ene with an equimolar amount of dimethyl diethyl malonate gives, when the procedure followed is as described for compound No. 17, a pulverulent polyester (compound No. 18) which sinters at about 135 and has an average molecular weight (vapour pressure method) of about 6,500.

EXAMPLE 15

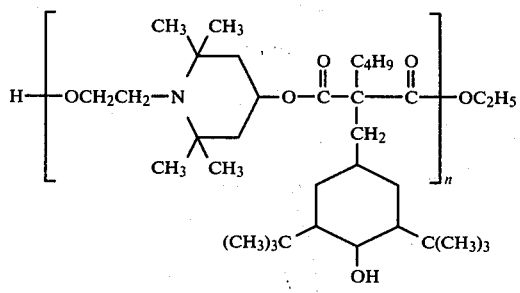

64.8 g (0.3 mol) of diethyl butylmalonate and 60 g of 1-(2-hydroxyethyl)-2,2,6,6-tetramethyl-4-hydroxy-piperidine were dissolved in 100 ml of xylene, the solution was warmed to 120° C. and 1.5 ml of tetraisobutyl oxotitanate were added. The temperature is kept at 130° C. for 3 hours and during this time the bulk of the ethanol distils off.

The remainder of the ethanol and the solvent are distilled off under a waterpump vacuum.

300 ml of toluene are added to the polymeric residue, 79 g (0.3 mol) of N-(3,5-di-tert.-butyl-4-hydroxybenzyl)-dimethylamine are added to the mixture and the solution is warmed to the reflux temperature. After the addition of 0.5 g of LiNH$_2$, the elimination of dimethylamine starts and this has ended after 3 hours. The toluene solution is neutralised with acetic acid and, when it has cooled to room temperature, the toluene solution is filtered and the filtrate is added dropwise to 1 l of ice-cold methanol. The polymer which then precipitates is filtered off and dried in vacuo at 80° C. (Compound No. 19) softening point 145° C.

EXAMPLE 16

100 parts of polypropylene powder (Moplen, fibre grade, from Messrs, Montedison) are homogenised with 0.2 part of octadecyl β-(3,5-di-tert.-butyl-4-hydroxyphenyl)-propionate and 0.25 part of a stabiliser from the table which follows, at 200° C. for 10 minutes in a Brabender plastograph. The composition thus obtained is withdrawn as rapidly as possible from the kneader and pressed in a toggle press to give a sheet 2–3 mm thick. A part of the raw pressing obtained is cut out and pressed between two high-gloss hard aluminium foils, by means of a manual hydraulic laboratory press, at 260° under a pressure of 12 tons for 6 minutes to give a 0.5 mm thick film which is immediately quenched in cold water. The 0.1 mm thick test film is prepared from this 0.5 mm film under exactly the same conditions. Sections of 60×44 mm each are then punched from this test film and exposed in a Xenotest 150. These test specimens are taken from the exposure apparatus at regular intervals and tested for their carbonyl content at 5.85μ in an IR spectrophotometer. The increase in the carbonyl extinction during exposure is a measure for the photo-oxidative degradation of the polymer [see L. Balaban et al., J. Polymer Sci., Part C, 22, 1059–1071 (1969)] and, as experience shows, this is related to a deterioration of the mechanical properties of the polymer. The time until a carbonyl extinction of about 0.30 is reached, at which point the comparison film is brittle, is taken as a measure of the protective action.

The protective action of the stabilisers according to the invention can be seen from the table which follows:

TABLE

| Compound No. | Exposure time in hours up to a carbonyl extinction of 0.300 |
|---|---|
| without light stabiliser | 1,400 |

TABLE-continued

| Compound No. | Exposure time in hours up to a carbonyl extinction of 0.300 |
|---|---|
| 1 | 8,130 |
| 3 | 9,040 |
| 5 | 5,060 |
| 10 | 8,600 |
| 11 | 8,600 |
| 12 | 13,200 |

What is claimed is:

1. A polysilylester of the formula

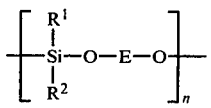

wherein n denotes a value of from 2 to about 50, E represents a divalent organic radical which contains a polyalkylpiperidine radical of the formula

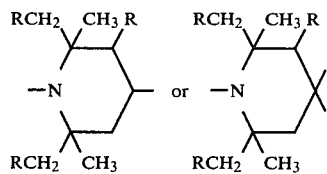

or is substituted by a polyalkylpiperidine side group of the formula

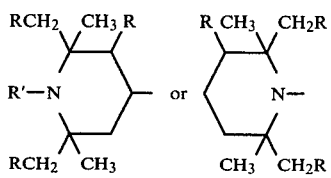

in which R denotes hydrogen or alkyl with 1-5 C atoms and R' denotes hydrogen, alkyl with 1-12 C atoms, alkenyl with 3-8 C atoms, alkinyl with 3-6 C atoms, aralkyl with 7-12 C atoms, alkanoyl with 1-8 C atoms or alkenoyl with 3-5 C atoms and $R^1$ and $R^2$ represent methyl, ethyl or phenyl, or a copolymer thereof with a polyalkylpiperidine-free component.

2. A polysilylester according to claim 1, the recurrent molecular unit of which contains a polyalkylpiperidine radical of the formula

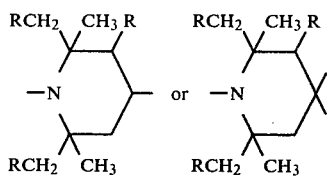

or is substituted by a polyalkylpiperidine side group of the formula

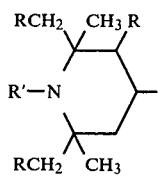

in which R denotes hydrogen or an alkyl radical with 1-5 C atoms and R' denotes hydrogen, alkyl with 1-12 C atoms, allyl, benzyl, acetyl, acryloyl or crotonyl.

3. A polysilylester according to claim 1 of the general formula III, in which $R^1$ and $R^2$ independently of one another denote methyl, ethyl or phenyl and E represents one of the radicals of the formula XVIII to XXX:

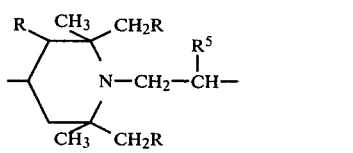

XVIII

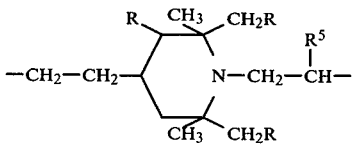

XIX

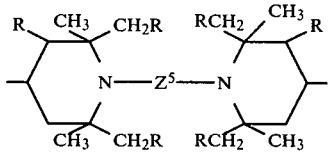

XX

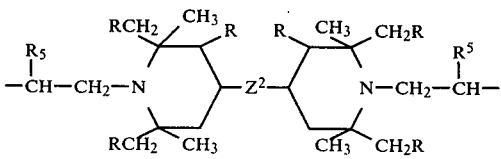

XXI

-continued

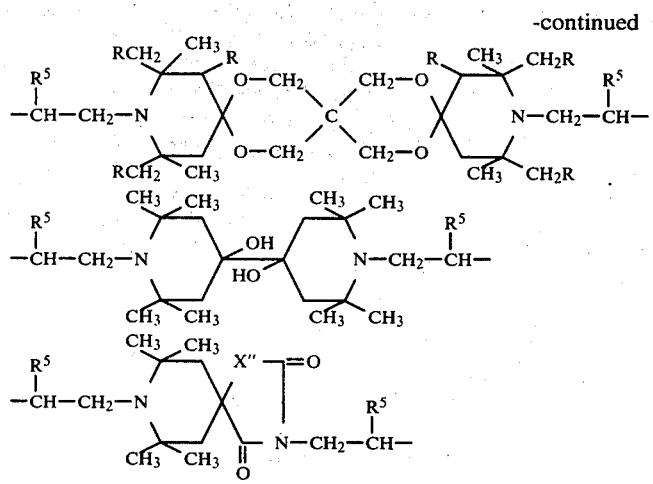

XXII

XXIII

XXIV

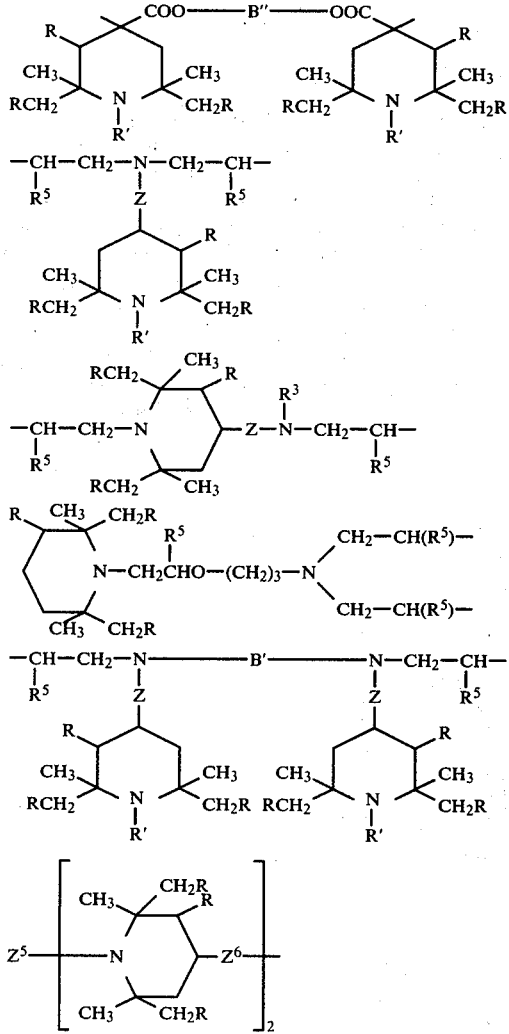

XXV

XXVI

XXVII

XXVIII

XXIX

XXX in which R denotes hydrogen or alkyl with 1–5 C atoms, R' denotes hydrogen, alkyl with 1–12 C atoms, allyl, benzyl, acetyl, acryloyl or crotonyl, X" is oxygen or NH, Z denotes a direct bond, —CH$_2$CH$_2$— or —OCH$_2$CH$_2$CH$_2$—, Z$^2$ denotes one of the radicals —N(R")—, —NR$^3$—CO—NR$^3$—, —NR$^3$—CO—CO—NR$^3$—, —NR$^3$—CO—Z-$^3$—CO—NR$^3$—, alkylene with 4–10 C atoms, p-xylylene,

—O—alkylene—O— with 1–10 C atoms, —O—alkylene—O— with 4–8 C atoms or —O—xylylene—O—, in which $R^3$ denotes hydrogen, alkyl with 1–12 C atoms, cyclohexyl, benzyl, or aryl with 6–14 C atoms, R″ denotes alkanoyl with 1–8 C atoms or alkenoyl with 3–5 C atoms and $Z^3$ denotes alkylene with 1–10 C atoms or phenylene, and B′ represents an alkylene radical with 2–12 C atoms, a xylylene or hexahydroxylylene radical, a cyclohexylene or 4,4′-dicyclohexylmethane radical, an arylene radical with 6–12 C atoms or a -phenylene-$Z^4$-phenylene- radical, in which $Z^4$ denotes —CH$_2$—, C(CH$_3$)$_2$, —O— or —SO$_2$—, $R^5$ is hydrogen, methyl or phenyl, $Z^5$ represents alkylene or alkenylene with 4–8 C atoms, p-xylylene or a group of the formula

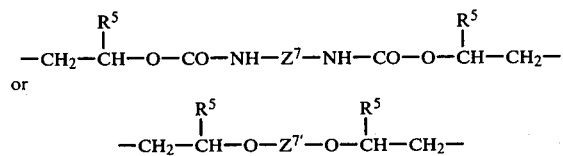

$Z^6$ represents one of the groups —CH$_2$CH$_2$—, —OCH$_2$CH($R^5$)—N($R^3$)—CH$_2$—CH($R^5$)—, —CH$_2$CH$_2$—N($R^3$)—CH$_2$CH($R^5$)— or —O—(CH$_2$)$_3$—N($R^3$)—CH$_2$CH($R^5$)—, $Z^7$ is alkylene with 2–12 C atoms, arylene with 6–12 C atoms, 4,4′-dicyclohexylenemethane or a radical -phenylene-$Z^4$-phenylene-, $Z^{7'}$ denotes alkylene or alkenylene with 4–8 C atoms or p-xylylene and B″ denotes an alkylene radical with 2–12 C atoms, an alkenylene radical with 4–8 C atoms, a xylylene or hexahydroxylylene radical, a cyclohexylene radical or a radical of the formula —CH$_2$CH$_2$OCH$_2$CH$_2$— or —CH$_2$CH$_2$O—phenylene—OCH$_2$CH$_2$—.

4. A copolymer according to claim 1, which consists of one of the structural units listed in claim 53 and a polyalkylpiperidine-free structural unit.

5. A copolymer according to claim 4, in which the proportion of the polyalkylpiperidine-free component is at most 50 mol %.

6. A polysilylester according to claim 1 in which R is hydrogen or methyl.

7. A polysilylester according to claim 1 in which R is hydrogen.

8. A polysilylester according to claim 3 in which R′ denotes hydrogen or methyl.

9. A polysilylester according to claim 8 in which R′ is hydrogen.

10. A plastic stabilised against photodegradation which contains 0.005 to 5% by weight of at least one polysilylester of claim 1.

11. A stabilised plastic according to claim 10 which contains 0.01 to 1 by weight of the polymeric stabiliser.

12. A stabilised plastic according to claim 10 or 11 which additionally contains yet a further stabiliser or other additives customary in plastics technology.

13. A stabilized plastic according to claim 11 which contains 0.02 to 0.5% by weight of the polymeric stabilizer.

14. A stabilised plastic according to claims 10 or 14 said plastic being selected from the group consisting of polyolefine, styrene polymer, polyurethane or polyamide.

* * * * *